US009873878B2

(12) United States Patent
Bodduluri et al.

(10) Patent No.: US 9,873,878 B2
(45) Date of Patent: Jan. 23, 2018

(54) COMPOSITIONS AND METHODS FOR USE IN TREATING SILICOSIS AND LUNG CANCER

(71) Applicant: University of Louisville Research Foundation, Inc., Louisville, KY (US)

(72) Inventors: Haribabu Bodduluri, Louisville, KY (US); Shuchismita R. Satpathy, Louisville, KY (US); Venkatakrishna R. Jala, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 15/085,359

(22) Filed: Mar. 30, 2016

(65) Prior Publication Data

US 2016/0289688 A1    Oct. 6, 2016

Related U.S. Application Data

(60) Provisional application No. 62/140,318, filed on Mar. 30, 2015, provisional application No. 62/147,421, filed on Apr. 14, 2015.

(51) Int. Cl.
*C12N 15/00* (2006.01)
*C12N 15/113* (2010.01)

(52) U.S. Cl.
CPC ...... *C12N 15/1138* (2013.01); *C12N 2310/14* (2013.01); *C12N 2320/30* (2013.01)

(58) Field of Classification Search
CPC .................................................. C12N 15/1138
See application file for complete search history.

(56) References Cited

U.S. PATENT DOCUMENTS

2011/0059885 A1* 3/2011 Lea .......................... A61K 38/04
                                                               514/1.4
2011/0301225 A1* 12/2011 Admyre ............. A61K 31/7088
                                                                514/44 R

OTHER PUBLICATIONS

Izumo et al., (Eur Repir J. Dec. 2009;34(6):1444-51).*
Adamson et al., (Am J Pathol. Oct. 1984;117(1):37-43).*
Kishikawa et al., (Prostaglandins. Oct. 1992;44(4):261-75. Abstract only).*
Sato et al., (Am J Physiol. Jun. 1999;276(6 Pt 1):L941-50, Abstract only).*
Mantovani, A., et al., Cancer-related inflammation. Nature, 2008. 454(7203): p. 436-44.
Houghton, A.M., Mechanistic links between COPD and lung cancer. Nat Rev Cancer, 2013. 13(4): p. 233-45.
Colotta, F., et al., Cancer-related inflammation, the seventh hallmark of cancer: links to genetic instability. Carcinogenesis, 2009. 30(7): p. 1073-81.
Russo, M., F. Di Nicolantonio, and A. Bardelli, Climbing RAS, the everest of oncogenes. Cancer Discov, 2014.4(1): p. 19-21.
Ji, H., et al., K-ras activation generates an inflammatory response in lung tumors. Oncogene, 2006. 25(14): p. 2105-12.

(Continued)

*Primary Examiner* — Cherie M Stanfield
(74) *Attorney, Agent, or Firm* — Stites & Harbison, PLLC; Mandy Wilson Decker

(57) ABSTRACT

A method for treating an inflammatory disease is provided. The method comprises administering an effective amount of a BLT1 inhibitor to a subject in need thereof. The BLT1 inhibitor is selected from the group consisting of a BLT1 receptor antagonist, a small molecule, a polypeptide, an siRNA, or a combination thereof.

8 Claims, 25 Drawing Sheets

(56) References Cited

OTHER PUBLICATIONS

Elinav, E., et al., Inflammation-induced cancer: crosstalk between tumours, immune cells and microorganisms. Nat Rev Cancer, 2013. 13(11): p. 759-71.
Takahashi, H., et al., Tobacco smoke promotes lung tumorigenesis by triggering IKKbeta- and JNK1-dependent inflammation. Cancer Cell, 2010. 17(1): p. 89-97.
Leung, C.C., I.T. Yu, and W. Chen, Silicosis. Lancet, 2012. 379(9830): p. 2008-18.
Huaux, F., New developments in the understanding of immunology in silicosis. Current opinion in allergy and clinical immunology, 2007. 7(2): p. 168-73.
Takato, H., et al., The specific chymase inhibitor TY-51469 suppresses the accumulation of neutrophils in the lung and reduces silica-induced pulmonary fibrosis in mice. Exp Lung Res, 2011. 37(2): p. 101-8.
Brown, T., Silica exposure, smoking, silicosis and lung cancer—complex interactions. Occup Med (Lond), 2009. 59(2): p. 89-95.
Cox, L.A., Jr., An exposure-response threshold for lung diseases and lung cancer caused by crystalline silica. Risk Anal, 2011. 31(10): p. 1543-60.
Liu, Y., et al., Exposure-response analysis and risk assessment for lung cancer in relationship to silica exposure: a 44-year cohort study of 34,018 workers. Am J Epidemiol, 2013. 178(9): p. 1424-33.
Kachuri, L., et al., Occupational exposure to crystalline silica and the risk of lung cancer in Canadian men. Int J Cancer, 2013.
Balkwill, F., Cancer and the chemokine network. Nat Rev Cancer, 2004.4(7): p. 540-50.
Ruffini, P.A., et al., Manipulating the chemokine-chemokine receptor network to treat cancer. Cancer, 2007. 109(12): p. 2392-404.
Oyoshi, M.K., et al., Leukotriene B4-driven neutrophil recruitment to the skin is essential for allergic skin inflammation. Immunity, 2012. 37(4): p. 747-58.
Li, R.C., B. Haribabu, S.P. Mathis, J. Kim, and D. Gozal, Leukotriene B4 receptor-1 mediates intermittent hypoxia-induced atherogenesis. Am J Respir Crit Care Med, 2011. 184(1): p. 124-31.
Chou, R.C., et al., Lipid-cytokine-chemokine cascade drives neutrophil recruitment in a murine model of inflammatory arthritis. Immunity, 2010. 33(2): p. 266-78.
Johnson, L., et al., Somatic activation of the K-ras oncogene causes early onset lung cancer in mice. Nature, 2001. 410(6832): p. 1111-6.
Houghton, A.M., et al., Neutrophil elastase-mediated degradation of IRS-1 accelerates lung tumor growth. Nature medicine, 2010. 16(2): p. 219-23.
Gong, L., et al., Promoting effect of neutrophils on lung tumorigenesis is mediated by CXCR2 and neutrophil elastase. Mol Cancer, 2013. 12(1): p. 154.
Wislez, M., et al., High expression of ligands for chemokine receptor CXCR2 in alveolar epithelial neoplasia induced by oncogenic kras. Cancer Res, 2006. 66(8): p. 4198-207.
Grivennikov, S.I., F.R. Greten, and M. Karin, Immunity, inflammation, and cancer. Cell, 2010. 140(6): p. 883-99.
Brown, J.M., et al., Silica-directed mast cell activation is enhanced by scavenger receptors. Am J Respir Cell Mol Biol, 2007. 36(1): p. 43-52.
Hicks, A., et al., Leukotriene B4 receptor antagonists as therapeutics for inflammatory disease: preclinical and clinical development. Expert Opin. Investig. Drugs, 2007. 16 (12): p. 1909-1920.
Bode, C., et al., Suppressive oligodeoxynucleotides reduce lung cancer susceptibility in mice with silicosis. Carcinogenesis, 2014. 35(5): p. 1078-83.
Hamilton, R.F., Jr., S.A. Thakur, and A. Holian, Silica binding and toxicity in alveolar macrophages. Free Radic Biol Med, 2008. 44(7): p. 1246-58.
Suzuki, N., et al., Mast cells are essential for the full development of silica-induced pulmonary inflammation: a study with mast cell-deficient mice. Am J Respir Cell Mol Biol, 1993. 9(5): p. 475-83.
Beamer, C.A., et al., Innate immune processes are sufficient for driving silicosis in mice. J Leukoc Biol, 2010. 88(3): p. 547-57.
Piguet, P.F., et al., Requirement of tumour necrosis factor for development of silica-induced pulmonary fibrosis. Nature, 1990. 344(6263): p. 245-7.
Yao, S.Q., et al., Role of Fas/FasL pathway-mediated alveolar macrophages releasing inflammatory cytokines in human silicosis. Biomed Environ Sci, 2013. 26(11): p. 930-3.
Chen, Y., et al., Neutralization of interleukin-17A delays progression of silica-induced lung inflammation and fibrosis in C57BL/6 mice. Toxicol Appl Pharmacol, 2014. 275(1): p. 62-72.
Cassel, S.L, et al., The Nalp3 inflammasome is essential for the development of silicosis. Proc Natl Acad Sci U S A, 2008. 105(26): p. 9035-40.
Wang, X., et al., Silencing CD36 gene expression results in the inhibition of latent-TGF-beta1 activation and suppression of silica-induced lung fibrosis in the rat. Respir Res, 2009. 10: p. 36.
Dostert, C., et al., Innate immune activation through Nalp3 inflammasome sensing of asbestos and silica. Science, 2008. 320(5876): p. 674-7.
Guo, J., et al., Neutralization of interleukin-1 beta attenuates silica-induced lung inflammation and fibrosis in C57BL/6 mice. Arch Toxicol, 2013. 87(11): p. 1963-73.
Hornung, V., et al., Silica crystals and aluminum salts activate the NALP3 inflammasome through phagosomal destabilization. Nature immunology, 2008. 9(8): p. 847-56.
Lammermann, T., et al., Neutrophil swarms require LTB4 and integrins at sites of cell death in vivo. Nature, 2013. 498(7454): p. 371-5.
Fridlender, Z.G. and S.M. Albelda, Tumor-associated neutrophils: friend or foe? Carcinogenesis, 2012. 33(5): p. 949-55.
Gregory, A.D. and A.M. Houghton, Tumor-associated neutrophils: new targets for cancer therapy. Cancer Res, 2011. 71(7): p. 2411-6.
Mantovani, A., et al., Neutrophils in the activation and regulation of innate and adaptive immunity. Nat Rev Immunol, 2011. 11(8): p. 519-31.
Shang, K., et al., Crucial involvement of tumor-associated neutrophils in the regulation of chronic colitis-associated carcinogenesis in mice. PLoS One, 2012. 7(12): p. e51848.
Tazzyman, S., et al., Inhibition of neutrophil infiltration into A549 lung tumors in vitro and in vivo using a CXCR2-specific antagonist is associated with reduced tumor growth. Int J Cancer, 2011. 129(4): p. 847-58.
Ilie, M., et al., Predictive clinical outcome of the intratumoral CD66b-positive neutrophil-to-CD8-positive T-cell ratio in patients with resectable nonsmall cell lung cancer Cancer, 2012. 118(6): p. 1726-37.
Carpagnano, G.E., et al., Neutrophilic airways inflammation in lung cancer: the role of exhaled LTB-4 and IL-8. BMC Cancer, 2011. 11: p. 226.
Sin, Y.M., et al., Mast cells in newly formed lining tissue during acute inflammation: a six day air pouch model in the mouse. Ann Rheum Dis, 1986.45(10): p. 873-7.
Zhang, L., et al., A novel immunocompetent murine model for replicating oncolytic adenoviral therapy. Cancer Gene Ther, 2015. 22(1): p. 17-22.
Nikitin, A.Y., et al., Classification of proliferative pulmonary lesions of the mouse: recommendations of the mouse models of human cancers consortium. Cancer research, 2004. 64(7): p. 2307-16.
Mathis, S.P., et al., Nonredundant roles for leukotriene B4 receptors BLT1 and BLT2 in inflammatory arthritis. J Immunol, 2010. 185(5): p. 3049-56.
Jala, V.R. and B. Haribabu, Real-time analysis of G protein-coupled receptor signaling in live cells. Methods Mol Biol, 2006. 332: p. 159-65.
Jala, V.R. and B. Haribabu, Real-time imaging of leukotriene B mediated cell migration and BLT1 interactions with beta-arrestin. J Vis Exp, 2010(46).
Haribabu, B., D.V. Zhelev, B.C. Pridgen, R.M. Richardson, H. Ali, and R. Snyderman, Chemoattractant receptors activate distinct pathways for chemotaxis and secretion. Role of G-protein usage. J Biol Chem, 1999. 274(52): p. 37087-92.
Jala, V.R., W.H. Shao, and B. Haribabu, Phosphorylation-independent beta-arrestin translocation and internalization of leukotriene B4 receptors. J Biol Chem, 2005. 280(6): p. 4880-7.

(56) References Cited

OTHER PUBLICATIONS

Basu, S., V.R. Jala, S. Mathis, S.T. Rajagopal, A. Del Prete, P. Maturu, J.O. Trent, and B. Haribabu, Critical role for polar residues in coupling leukotriene B4 binding to signal transduction in BLT1. J Biol Chem, 2007. 282(13): p. 10005-17.

Haribabu, B., M.W. Verghese, D.A. Steeber, D.D. Sellars, C.B. Bock, and R. Snyderman, Targeted disruption of the leukotriene B(4) receptor in mice reveals its role in inflammation and platelet-activating factor-induced anaphylaxis,. J Exp Med, 2000. 192(3): p. 433-8.

Shao, W.H., A. Del Prete, C.B. Bock, and B. Haribabu, Targeted disruption of leukotriene B4 receptors BLT1 and BLT2: a critical role for BLT1 in collagen-induced arthritis in mice, J Immunol, 2006. 176(10): p. 6254-61.

Miyahara, N., H. Ohnishi, H. Matsuda, S. Miyahara, K Takeda, T. Koya, S. Matsubara, M. Okamoto, A. Dakhama, B. Haribabu, and E.W. Gelfand, Leukotriene B4 receptor 1 expression on dendritic cells is required for the development of Th2 responses and allergen-induced airway hyperresponsiveness. J Immunol, 2008. 181(2): p. 1170-8.

Ohnishi, H., N. Miyahara, A. Dakhama, K. Takeda, S. Mathis, B. Haribabu, and E.W. Gelfand, Corticosteroids enhance CD8+ T cell-mediated airway hyperresponsiveness and allergic inflammation by upregulating leukotriene B4 receptor 1. J Allergy Clin Immunol, 2008. 121(4): p. 864-71 e4.

Spite, M., J. Hellmann, Y. Tang, S.P. Mathis, M. Kosuri, A. Bhatnagar, V.R. Jala, and B. Haribabu, Deficiency of the leukotriene B4 receptor, BLT-1, protects against systemic insulin resistance in diet-induced obesity. J Immunol, 2011. 187(4): p. 1942-9.

Jala, V.R. and B. Haribabu, Leukotrienes and atherosclerosis: new roles for old mediators. Trends Immunol, 2004. 25(6): p. 315-22.

Haribabu, B., Leukotrienes: Novel targets for vascular disease. Discov Med, 2004.4(23): p. 281-7.

Subbarao, K., V.R. Jala, S. Mathis, J. Suttles, W. Zacharias, J. Ahamed, H. Ali, M.T. Tseng, and B. Haribabu, Role of leukotriene B4 receptors in the development of atherosclerosis: potential mechanisms. Arterioscler Thromb Vasc Biol, 2004. 24(2): p. 369-75.

Miyahara, N., K. Takeda, S. Miyahara, S. Matsubara, T. Koya, A. Joetham, E. Krishnan, A. Dakhama, B. Haribabu, and E.W. Gelfand, Requirement for leukotriene B4 receptor 1 in allergen-induced airway hyperresponsiveness. Am J Respir Crit Care Med, 2005. 172(2): p. 161-7.

Del Prete, A., W.H. Shao, S. Mitola, G. Santoro, S. Sozzani, and B. Haribabu, Regulation of dendritic cell migration and adaptive immune response by leukotriene B4 receptors: a role for LTB4 in up-regulation of CCR7 expression and function. Blood, 2007. 109(2): p. 626-31.

Mathis, S., V.R. Jala, and B. Haribabu, Role of leukotriene B4 receptors in rheumatoid arthritis. Autoimmun Rev, 2007. 7(1): p. 12-7.

Liao, T., Y. Ke, W.H. Shao, B. Haribabu, H.J. Kaplan, D. Sun, and H. Shao, Blockade of the interaction of leukotriene b4 with its receptor prevents development of autoimmune uveitis. Invest Ophthalmol Vis Sci, 2006. 47(4): p. 1543-9.

Scott, M.J., W.G. Cheadle, J.J. Hoth, J.C. Peyton, K. Subbarao, W.H. Shao, and B. Haribabu, Leukotriene B4 receptor (BLT-1) modulates neutrophil influx into the peritoneum but not the lung and liver during surgically induced bacterial peritonitis in mice. Clin Diagn Lab Immunol, 2004. 11(5): p. 936-41.

Allendorf, D.J., J. Yan, G.D. Ross, R.D. Hansen, J.T. Baran, K. Subbarao, L. Wang, and B. Haribabu, C5a-mediated leukotriene B4-amplified neutrophil chemotaxis is essential in tumor immunotherapy facilitated by anti-tumor monoclonal antibody and beta-glucan. J Immunol, 2005. 174(11): p. 7050-6.

\* cited by examiner

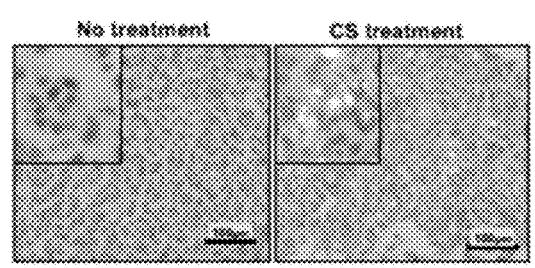
FIG. 2A        FIG. 2B
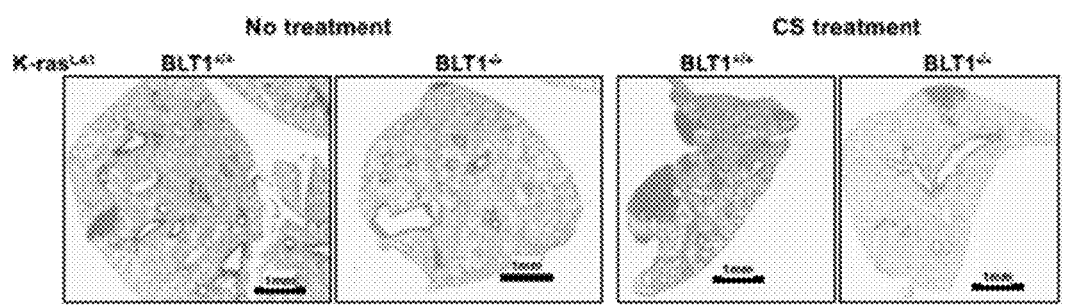
FIG. 2C
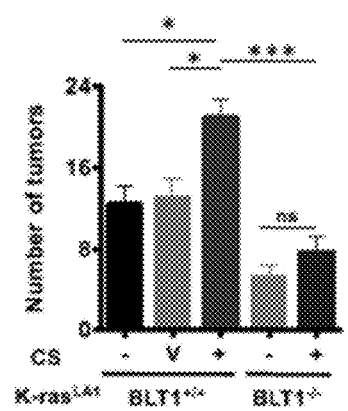
FIG. 2D

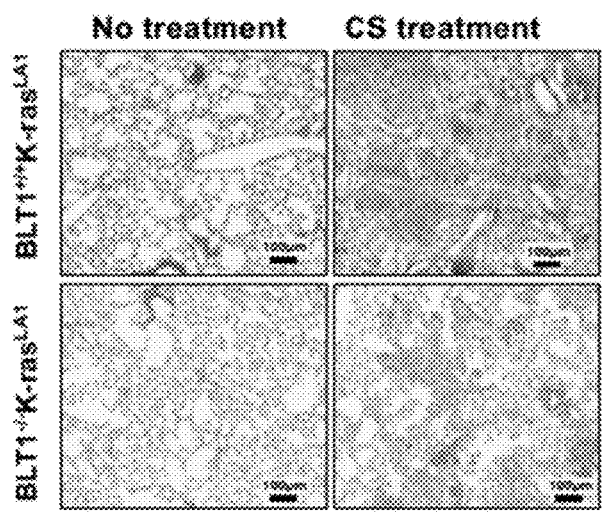
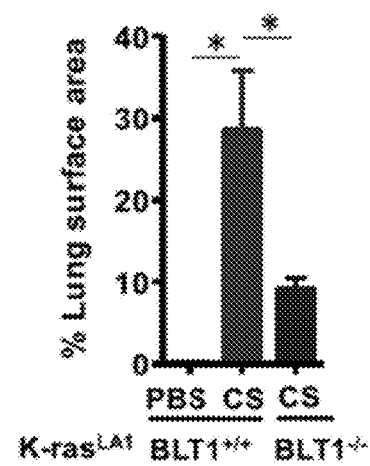
FIG. 3A
FIG. 3B
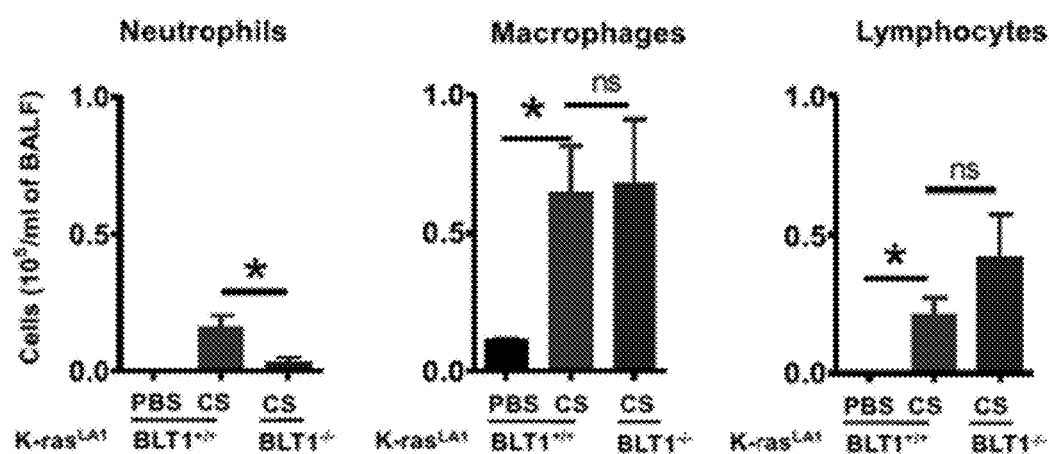
FIG. 3C

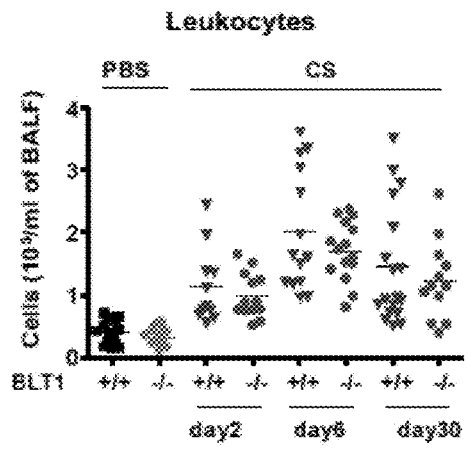
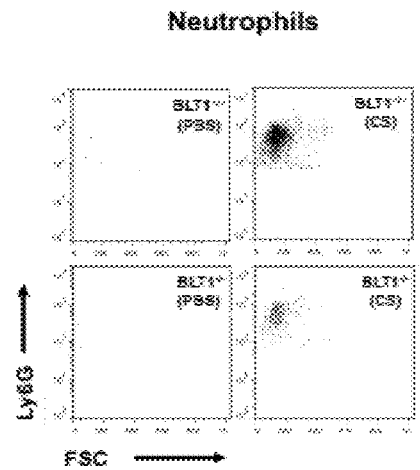
FIG. 5A
FIG. 5B
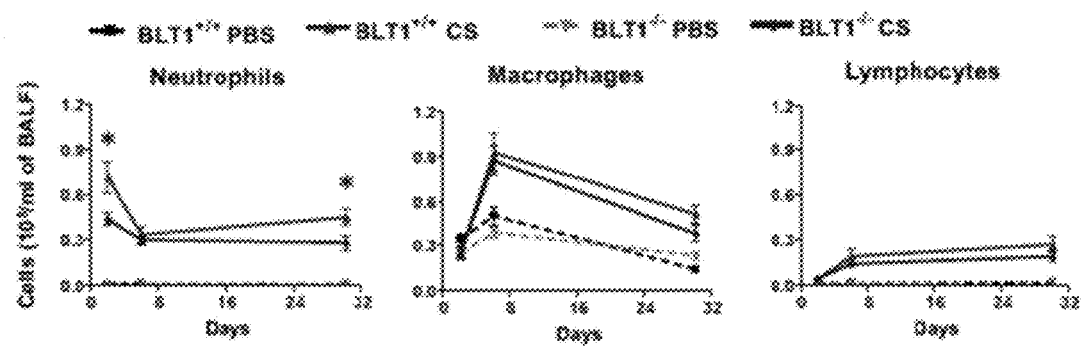
FIG. 5C
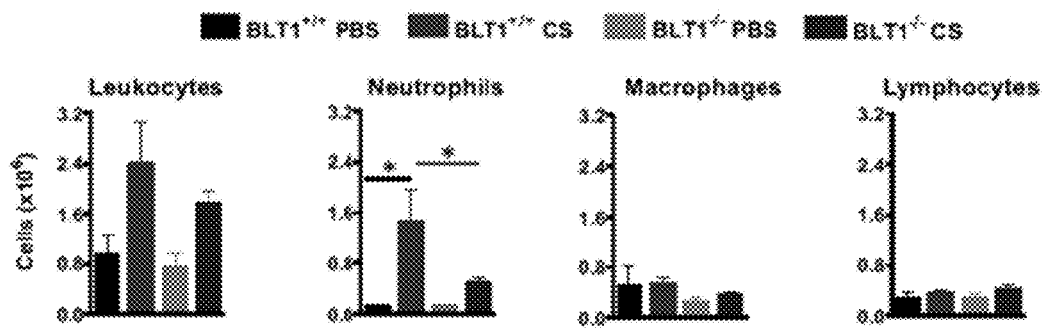
FIG. 5D

COMPOSITIONS AND METHODS FOR USE IN TREATING SILICOSIS AND LUNG CANCER

RELATED APPLICATIONS

This application claims priority from U.S. Provisional Application Ser. No. 62/140,318, filed Mar. 30, 2015, and U.S. Provisional Application Ser. No. 62/147,421, filed Apr. 14, 2015, the entire disclosures of which are incorporated herein by this reference.

GOVERNMENT INTEREST

This invention was made with government support under CA138623 awarded by the National Institutes of Health. The government has certain rights in the invention.

TECHNICAL FIELD

The presently-disclosed subject matter relates to treatment of silicosis, lung cancer, particularly inflammation-promoted lung cancer, and lung inflammatory disorders, using BLT1 inhibitors, including BLT1 receptor antagonists.

INTRODUCTION

Lung cancer is the single largest cause of cancer-related deaths worldwide. Chronic inflammation considered the seventh hallmark of cancer is promoted by a variety of intrinsic and extrinsic factors [1-3]. Intrinsic factors such as activating mutation of K-ras, often associated with human lung adenocarcinomas [4] induces a pro-inflammatory microenvironment [5]. Extrinsic factors such as cigarette smoke or air-borne pollutants commonly encountered in the environment, also promote chronic lung inflammation and cancer [6, 7].

Exposure to air-borne particulates such as crystalline silica (CS) is a major global occupational health hazard [8], encountered in diverse array of industrial settings such as mining, pottery, glass and concrete production. Around two million U.S workers and several million more worldwide are occupationally exposed to CS particles. CS exposure leads to lung infiltration of neutrophils, macrophages and lymphocytes causing lung inflammation and the problem is further compounded by massive lung fibrosis leading to the disease silicosis [9, 10]. Silicosis is irreversible and incurable due to impaired particle clearance resulting in persistent lung inflammation and may eventually lead to lung cancer [11, 12]. Epidemiological data suggests that smokers with silicosis are at even higher risk of lung cancer [13, 14]. Though the association of silicosis with lung cancer has been suspected for many decades, there were no established model systems to study mechanisms that link CS-induced chronic inflammation to lung cancer promotion.

Chemokines orchestrate a tightly regulated process of inflammatory cell recruitment to sites of tissue damage, which is a key step in the process of cancer-related inflammation [15, 16]. The lipid chemoattractant $LTB_4$ is one of the early mediators of inflammation. The high affinity $LTB_4$ receptor, BLT1 is predominantly expressed on peripheral blood leukocytes and is known to modulate many chronic inflammatory diseases such as arthritis, atherosclerosis, allergic inflammation and insulin resistance during diet-induced obesity [17-20].

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods of treating inflammatory diseases and/or disorders. Inflammatory diseases include, but are not limited to, arthritis, joint inflammation, atherosclerosis, sleep apnea, obesity induced inflammation, asthma, colon cancer, silicosis, lung cancer, a lung inflammatory disorder, or combinations thereof.

In some embodiments, the methods include administering an effective amount of a BLT1 inhibitor to a subject in need thereof. The BLT1 inhibitor may include a BLT1 receptor antagonist, a small molecule, a polypeptide, an siRNA, or a combination thereof. In some embodiments, the BLT1 inhibitor is provided in a pharmaceutical composition including a pharmaceutically acceptable carrier.

In some embodiments, the administering of an effective amount of a BLT1 inhibitor decreases or eliminates inflammation in the subject without causing immune deficiency.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1A depicts representative lung lobes of mice showing surface tumors; fewer tumors seen in $BLT1^{-/-}K\text{-}ras^{LA1}$ mice (n=17) when compared to $BLT1^{+/+}K\text{-}ras^{LA1}$ (n=13) mice; arrows point to tumors.

FIG. 1B depicts histological appearance of lung lesions: hyperplasia, adenomatous hyperplasia and adenoma of various sizes in lung sections of mice; scale bars, 100 μm.

FIG. 1C depicts quantification of hyperplasia, adenomatous hyperplasia and adenoma from serial lung sections in $BLT1^{+/+}K\text{-}ras^{LA1}$ (n=7) and $BLT1^{-/-}K\text{-}ras^{LA1}$ (n=7) mice; Hyperplasia (H); adenomatous hyperplasia (AH). Error bars in FIG. 1C denote mean±SEM. *P<0.03, **P<0.004. Mann Whitney U-test.

FIGS. 2A-D show that CS-promoted lung tumor progression is abrogated in the absence of BLT1. Forty five day old $BLT1^{+/+}K\text{-}ras^{LA1}$ and $BLT1^{-/-}K\text{-}ras^{LA1}$ mice were exposed to CS by intra-tracheal instillation as described in methods. Sixty days post CS instillation; lungs from these mice were analyzed for CS particle deposition and tumor multiplicity.

FIG. 2A depicts representative lung H&E sections showing deposited CS particles; scale bars, 100 μm; insets show CS particles at higher magnification.

FIG. 2B depicts lung CS exposure was determined based on semi-quantitative scoring (scale of 0-3) of CS particle deposition in sections; n=5 for both groups. Error bars denote mean±SEM.*P<0.025, ***P<0.0003, n.s is non-significant; Mann Whitney U-test.

FIG. 2C depicts representative lung lobe sections showing adenomas; scale bars, 1 mm.

FIG. 2D depicts quantification of adenomas from all serial lung sections of different groups of animals and treatments as indicated; V indicates vehicle (PBS) alone treatment. The number of mice in each group are, untreated $BLT1^{+/+}K-ras^{LA1}$ (n=7); PBS treated $BLT1^{+/+}K-ras^{LA1}$ (n=5); CS treated $BLT1^{+/+}K-ras^{LA1}$ (n=10); untreated $BLT1^{-/-}K-ras^{LA1}$ (n=7); CS treated $BLT1^{-/-}K-ras^{LA1}$ (n=10). Error bars denote mean±SEM.*P<0.025, ***P<0.0003, n.s is non-significant; Mann Whitney U-test.

FIGS. 3A-C show that absence of BLT1 attenuates lung inflammation in $K-ras^{LA1}$ mice. Lungs from $BLT1^{+/+}K-ras^{LA1}$ and $BLT1^{-/-}K-ras^{LA1}$ mice exposed to CS for 60 days were assessed for inflammation and inflammatory cell recruitment.

FIG. 3A depicts representative lung H&E sections showing inflammation post CS treatment; scale bars, 100 μm.

FIG. 3B depicts lung inflammation scored as the percentage of inflamed lung area to total lung area in H&E stained lung sections. The number of mice in each group are, PBS treated $BLT1^{+/+}K-ras^{LA1}$ (n=3); CS treated $BLT1^{+/+}K-ras^{LA1}$ (n=8); CS treated $BLT1^{-/-}K-ras^{LA1}$ (n=10). Error bars denote mean±SEM. *P<0.04 Mann Whitney U-test.

FIG. 3C depicts CS exposure induced recruitment of neutrophils, macrophages and lymphocytes into airways was assessed in whole lung lavage by flow cytometry as described in methods. The number of mice in each group are, PBS treated $BLT1^{+/+}K-ras^{LA1}$ (n=3); CS treated $BLT1^{+/+}K-ras^{LA1}$ (n=4); CS treated $BLT1^{-/-}K-ras^{LA1}$ (n=5). Error bars denote mean±SEM. *P<0.04 Mann Whitney U-test.

FIG. 4A depicts representative lung sections of mice showing macrophages identified by immuno-histochemical staining for F4/80 (macrophage marker); arrows point macrophages; scale bars, 300 μm.

FIG. 4B depicts quantification of macrophages in lung sections of untreated or CS treated $BLT1^{+/+}K-ras^{LA1}$ and $BLT1^{-/-}K-ras^{LA1}$ mice. Data represent 3 mice of each group; 5 independent fields per mouse lung section were randomly selected for macrophage counting and average macrophages per field were calculated. Error bars denote mean±SEM. ***P<0.0001.Unpaired t-test.

FIGS. 5A-D show attenuation of CS-induced lung neutrophil recruitment in the absence of BLT1. Eight weeks old $BLT1^{+/+}$ and $BLT1^{-/-}$ mice were exposed to CS. Inflammatory cell recruitment into airways (FIGS. 5A-C) and lung interstitium (FIG. 5D) was assessed by flow cytometry using surface staining for cell specific markers. The whole lung lavage was analyzed at the indicated times.

FIG. 5A depicts the number of total leukocytes; each dot represents a single mouse.

FIG. 5B depicts neutrophils 2 days post CS exposure in the flow-cytometry scatter plots.

FIG. 5C depicts the number of neutrophils, macrophages and lymphocytes. Data represent at least 11 mice per group; difference between CS treated $BLT1^{+/+}$ and $BLT1^{-/-}$ group is indicated.

FIG. 5D depicts analysis of unlavaged whole lung digests 2 days post CS exposure show number of total leukocytes, neutrophils, macrophages and lymphocytes. The number of mice in each group are, PBS treated $BLT1^{+/+}$ (n=3); CS treated $BLT1^{+/+}$ (n=5); PBS treated $BLT1^{-/-}$ (n=5); CS treated $BLT1^{-/-}$ (n=6). Error bars denote mean±SEM. *P<0.04 Mann Whitney U-test.

In FIGS. 6C-D, fold change of mRNA levels over PBS treated $BLT1^{+/+}$ samples are shown; differences in mRNA levels are not significant between the CS exposed $BLT1^{+/+}$ and $BLT1^{-/-}$ groups. Data represent at least 5 mice per group; error bars denote mean±SEM. *P<0.03, P<0.009, *P<0.0007; Unpaired t-test.

FIG. 6A shows $LTB_4$ levels in lung lavage fluids of CS exposed $BLT1^{+/+}$ and $BLT1^{-/-}$ mice at indicated times.

FIG. 6B shows $LTB_4$ levels in lung lavage fluids of $BLT1^{+/+}K-ras^{LA1}$ and $BLT1^{-/-}K-ras^{LA1}$ mice exposed to CS for 60 days.

FIG. 6C shows quantitative real-time PCR analysis of total lung RNA showing fold increase of neutrophil-active cytokines and chemokines in $BLT1^{+/+}$ and $BLT1^{-/-}$ mice exposed to CS for 2 days.

FIG. 6D shows quantitative real-time PCR analysis of total lung RNA showing fold increase of neutrophil-active cytokines and chemokines in $BLT1^{+/+}K-ras^{LA1}$ and $BLT1^{-/-}K-ras^{LA1}$ mice exposed to CS for 60 days.

FIG. 7A depicts microarray analysis of total lung RNA from $BLT1^{+/+}$ and $BLT1^{-/-}$ mice exposed to CS for 2 days.

FIG. 7B depicts microarray analysis of total lung RNA from $BLT1^{+/+}K-ras^{LA1}$ and $BLT1^{-/-}K-ras^{LA1}$ mice exposed to CS for 60 days.

FIG. 8A depicts analysis of whole lung lavage fluid in multiplex assay from $BLT1^{+/+}$ and $BLT1^{-/-}$ mice exposed to CS; PBS treated $BLT1^{+/+}$ (n=3); CS treated $BLT1^{+/+}$ (n=5); PBS treated $BLT1^{-/-}$ (n=5); and CS treated $BLT1^{-/-}$ (n=5) for 2 days; *P<0.01.

FIG. 8B depicts analysis of whole lung lavage fluid in multiplex assay from $BLT1^{+/+}K-ras^{LA1}$ and $BLT1^{-/-}K-ras^{LA1}$ mice exposed to CS; PBS treated $BLT1^{+/+}K-ras^{LA1}$ (n=3); CS treated $BLT1^{+/+}K-ras^{LA1}$ (n=4); and CS treated $BLT1^{-/-}K-ras^{LA1}$ (n=4) for 60 days.

In triplicate cultures 0.3×10⁶ of the indicated cell types were stimulated with 100 μg/cm² of CS for six hours. Alveolar macrophages and lung mast cells were purified as described in methods and exposed to CS in vitro. Purity of the cell types were determined by flow cytometry. Thioglycollate elicited neutrophils and macrophages; resident peritoneal macrophages; lung mast cells were ≥95% pure, whereas BMMC, BMDM and alveolar macrophages were ≥99% pure. Error bars denote mean±SEM. Data are representative of at least two independent experiments in triplicate cultures.

Figure 9A:
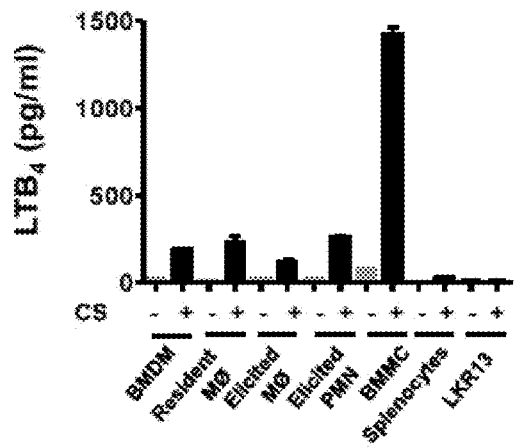
FIGS. 9A-D show cell type specificity of CS-induced $LTB_4$ and IL-1β production. Lung epithelial cell line (LKR13) and primary cells: macrophages, mast cells, neutrophils, splenocytes from wild-type (WT) were assessed for production of $LTB_4$ and IL-1β in vitro post CS stimulation.

FIG. 9A depicts $LTB_4$ levels in culture supernatants of CS exposed ex-vivo cultured immune cells and lung epithelial cell line (LKR13) as indicated; MO is macrophage, PMN is neutrophil, BMDM is bone-marrow derived macrophages, BMMC is bone-marrow derived mast cells.

Figure 9B:
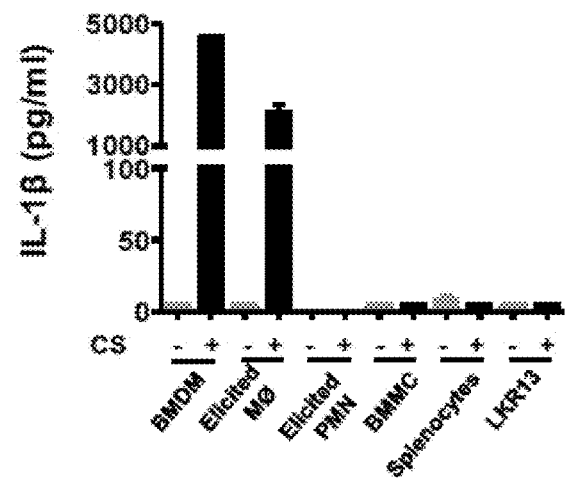

FIG. 9B depicts IL-1β levels in the same culture supernatants as in panel a.

Figure 9C:
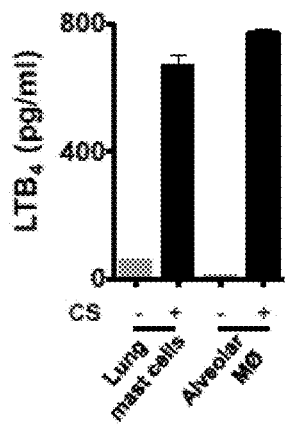

FIG. 9C depicts the CS-induced $LTB_4$ production in culture supernatants of alveolar macrophages and lung mast cells.

Figure 9D:
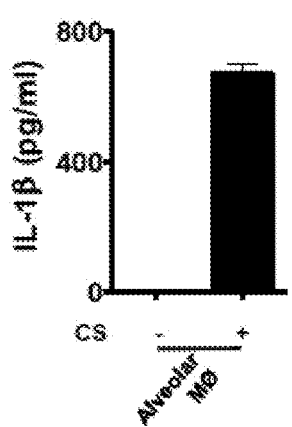

FIG. 9D depicts the CS-induced IL-1β production in culture supernatants of alveolar macrophages and lung mast cells.

Figure 10A:
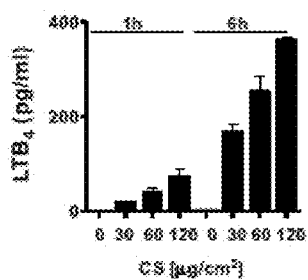

FIGS. 10A-E show that CS-induced $LTB_4$ production mediates neutrophil migration. $LTB_4$ production by CS treated RAW264.7 cells in vitro was analyzed and its ability to chemoattract neutrophils was assessed. Error bars denote mean±SEM; ***$P<0.0001$; Unpaired t-test. All data represent triplicate cultures and are representative of at least two independent experiments FIG. 10A depicts $LTB_4$ production by cells in vitro, measured in culture supernatants of RAW264.7 cells exposed to varying doses of CS for 6 h.

Figure 10B:
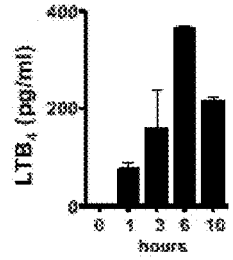

FIG. 10B depicts $LTB_4$ production by cells in vitro, measured in culture supernatants of RAW264.7 cells exposed to 120 μg/cm² CS for indicated times.

Figure 10C:
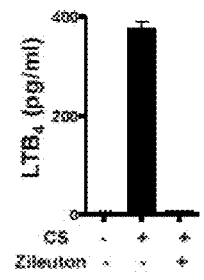

FIG. 10C depicts $LTB_4$ production by cells in vitro, measured in culture supernatants of RAW264.7 cells exposed to 120 μg/cm² CS for 6 h in presence of 5-LO inhibitor.

Figure 10D:
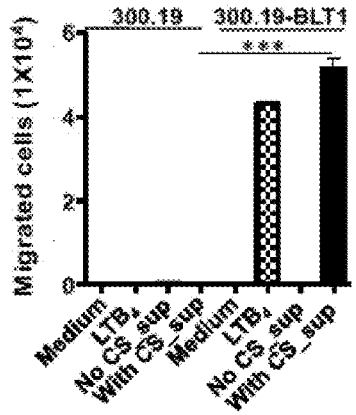

FIG. 10D depicts chemotaxis of parental or BLT1 expressing 300.19 cells. Cell supernatants without CS exposure labeled as "No CS_sup" and those exposed to 120 μg/cm² CS labeled as "With CS_sup."

Figure 10E:
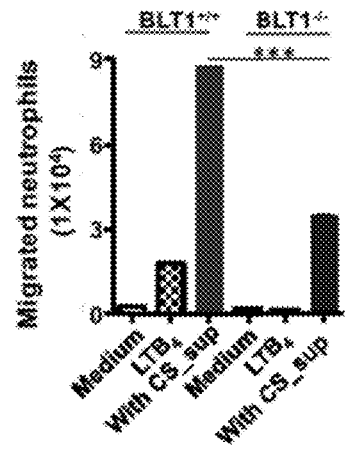

FIG. 10E depicts chemotaxis of BLT1⁺/⁺ or BLT1⁻/⁻ elicited peritoneal neutrophils (≥95% pure) to medium, $LTB_4$, supernatants (sup) from RAW264.7 cells exposed to 0 or 120 μg/cm² CS for 6 h. Cell supernatants exposed to 120 μg/cm² CS labeled as "With CS_sup."

Figure 11A:
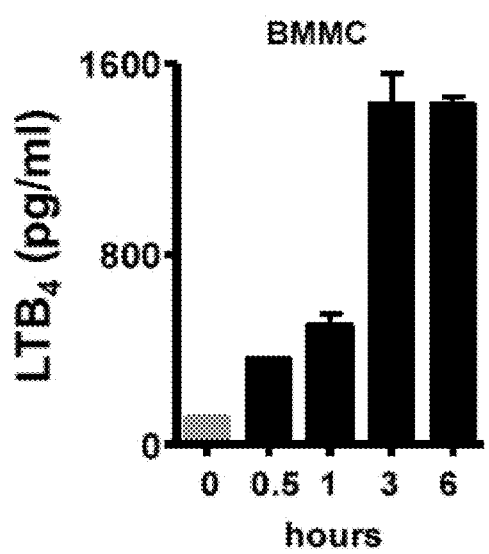
Figure 11B:
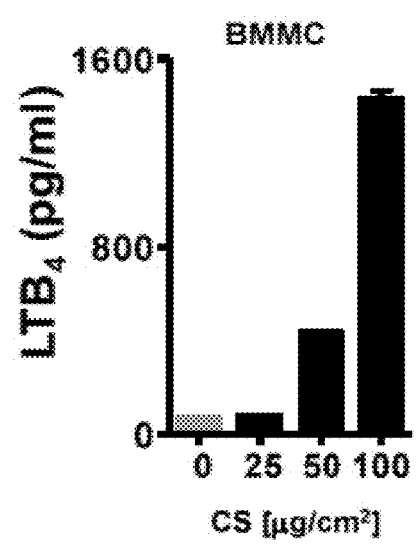

FIGS. 11A-B show $LTB_4$ production by bone-marrow derived mast cells (BMMC) under varying conditions. Data are representative of at least two independent experiments; error bars denote mean±SEM.

FIG. 11A depicts $LTB_4$ production by bone-marrow derived mast cells (BMMC) in response to 100 μg/cm² CS activation for indicated times.

FIG. 11B depicts $LTB_4$ production by bone-marrow derived mast cells (BMMC) in response to varying doses of CS for 6 hours.

Figure 12A:
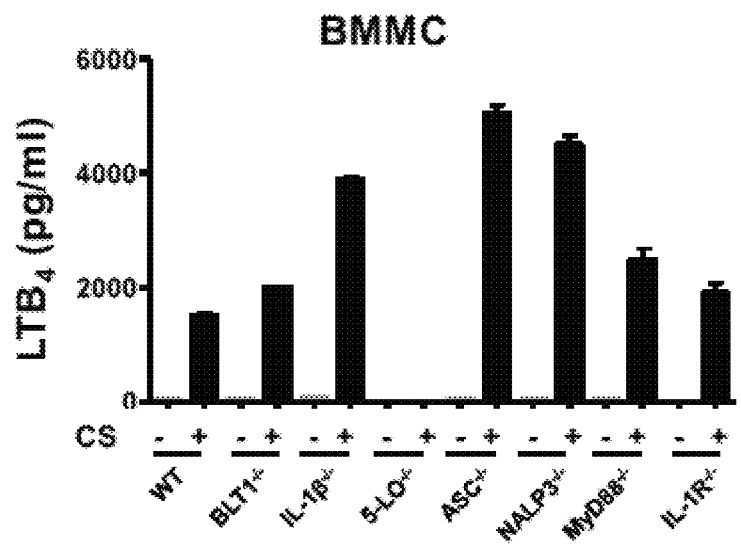
Figure 12B:
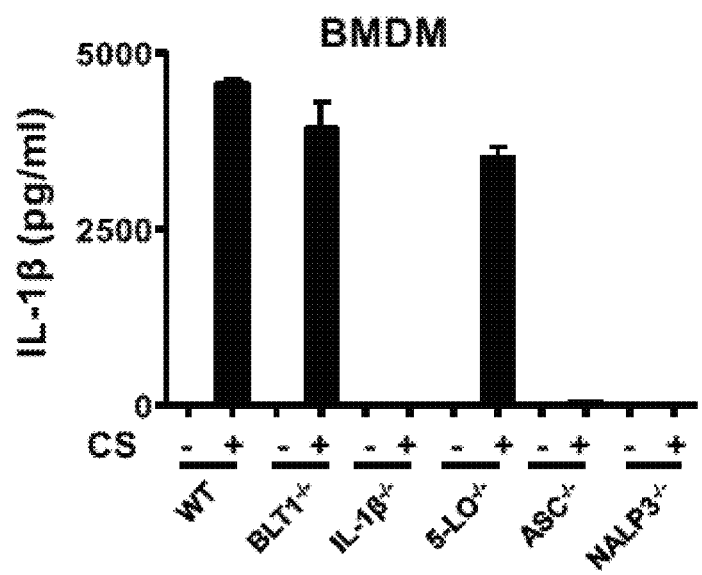

FIGS. 12A-B show independent regulation of $LTB_4$ and IL-1β production in CS exposed cells. Interdependence of CS-induced $LTB_4$ and IL-1β production was determined in cultured bone-marrow derived mast cells (BMMC) and bone-marrow derived macrophages (BMDM) from different gene knockout mice as indicated. Purity of the cells was determined by flow cytometry. All cell types of indicated genotypes were ≥99% pure. Error bars denote mean±SEM. Data are representative of at least two independent experiments performed in triplicate cultures.

FIG. 12A depicts EIA determined $LTB_4$ levels in triplicate cultures 0.3×10⁶ of BMMCs stimulated with 100 μg/cm² of CS for six hours.

FIG. 12B depicts ELISA determined IL-1β levels in triplicate cultures 0.3×10⁶ of BMDMs stimulated with 100 μg/cm² of CS for six hours.

Figure 13:
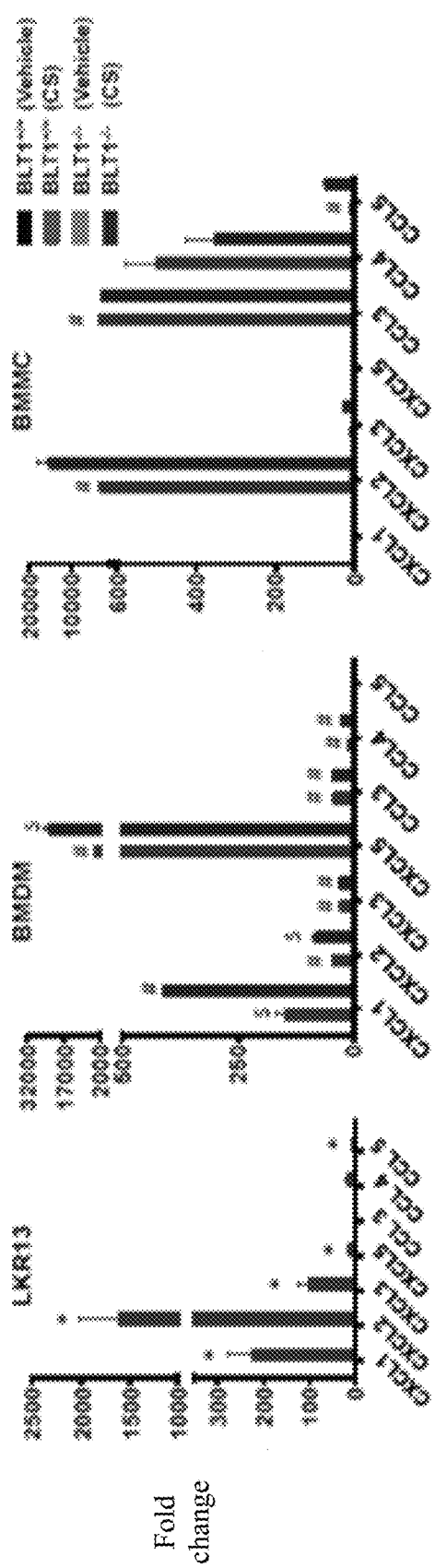

FIG. 13 shows Neutrophil-active chemokines production by CS exposed cells. Lung epithelial cell line (LKR13) and primary cells: bone-marrow derived macrophages (BMDM), bone-marrow derived mast cells (BMMC) were assessed for production of CXC/CC neutrophil chemokines in vitro. CC and CXC neutrophil-active chemokines up-regulated in CS exposed LKR13 and BMDM, BMMC from BLT1⁺/⁺ and BLT1⁻/⁻ mice were measured in total RNA and expressed as fold change over BLT1⁺/⁺ (vehicle) group. Error bars denote mean±SEM; $ denotes  and # denotes *. *$P<0.05$, $P<0.009$, *$P<0.0001$. Unpaired t-test.

Figure 14A:
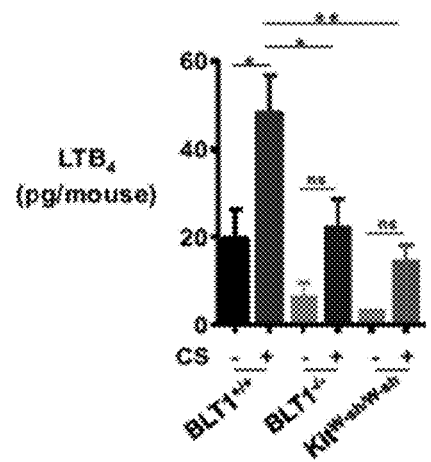
Figure 14B:
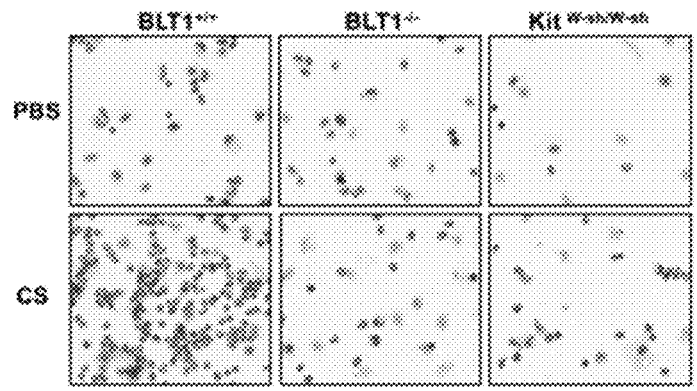
Figure 14C:
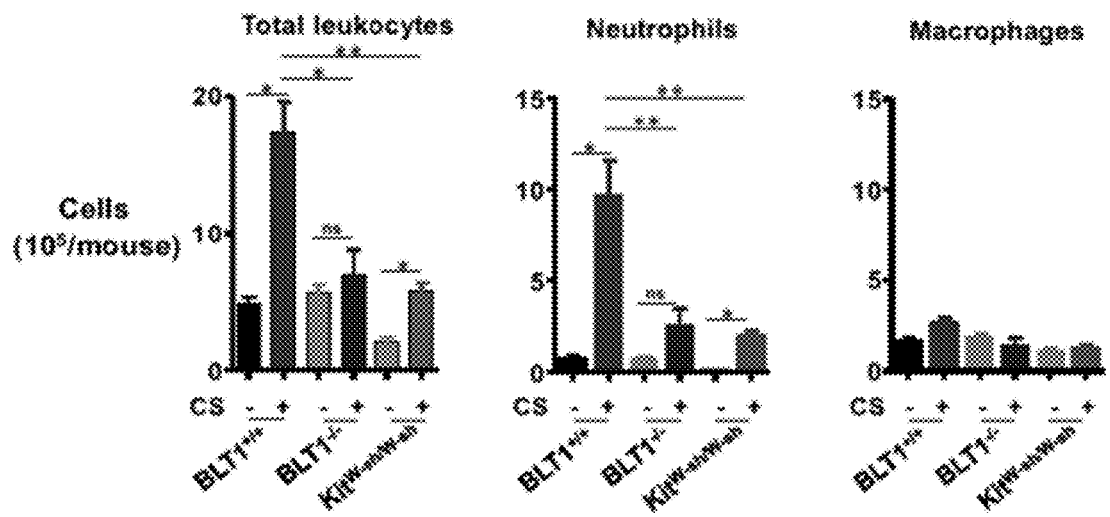

FIGS. 14A-C show CS-induced neutrophil recruitment into air pouch is dependent on $LTB_4$/BLT1 axis. CS induced inflammation in an air pouch was analyzed. Six hours post CS particle exposure the air pouch was lavaged with 3 ml of buffer to assess $LTB_4$ levels and infiltrating immune cells. Data are representative of at least five mice per group. Error bars denote mean±SEM. *$P<0.02$, **$P<0.009$; Mann Whitney U-test.

FIG. 14A depicts $LTB_4$ levels.

FIG. 14B depicts leukocytes on cytospin slides.

FIG. 14C depicts total leukocytes, neutrophils and macrophages as identified by flow cytometry of the air pouch lavage fluid from mice of the indicated genotypes.

Figure 15A:
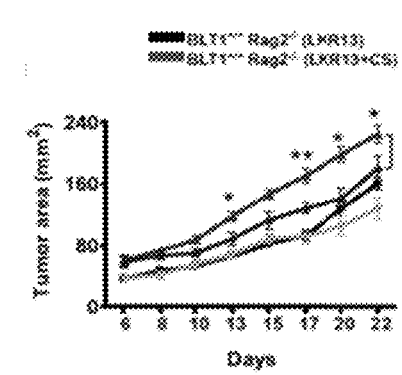
Figure 15B:
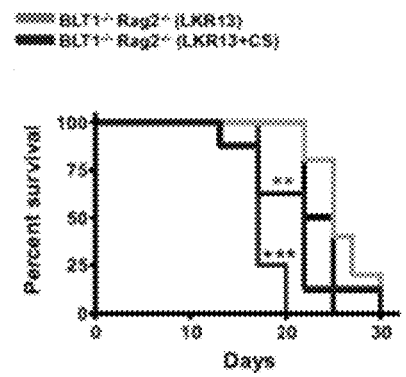
Figure 15C:
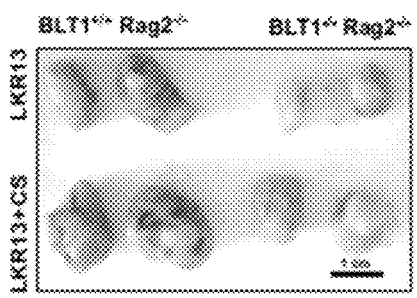
Figure 15D:
Figure 15E:
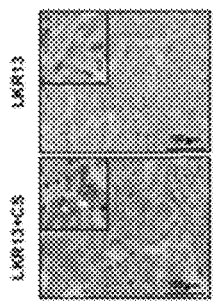
Figure 15F:
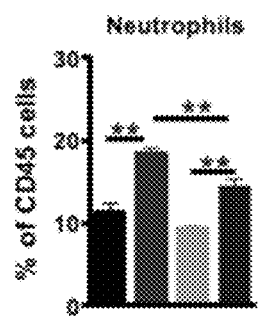
Figure 15F:
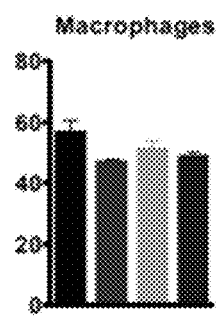
Figure 15F:
Figure 15G:
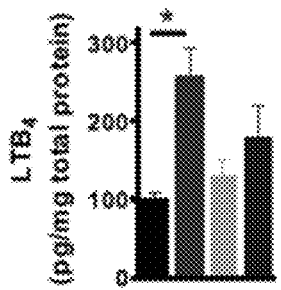
Figure 15H:
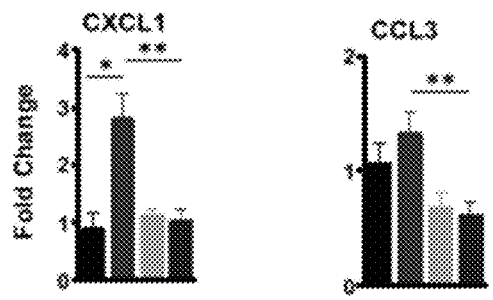

FIGS. 15A-H show absence of BLT1 protects from CS-promoted growth of implanted lung tumors. LKR13 cells along with CS particles were implanted subcutaneously into BLT1⁺/⁺Rag2⁻/⁻ or BLT1⁻/⁻Rag2⁻/⁻ mice and the kinetics of tumor growth, survival of mice and tumor inflammatory microenvironment was analyzed. In FIGS. 15F-H the number of mice in each group are, LKR13 injected BLT1⁺/⁺Rag2⁻/⁻ (n=4), LKR13 injected BLT1⁻/⁻Rag2⁻/⁻ (n=4), LKR13 with CS injected BLT1⁺/⁺Rag2⁻/⁻ (n=7) and LKR13 with CS injected BLT1⁻/⁻Rag2⁻/⁻ (n=7). Error bars denote mean±SEM. *$P<0.02$, $P<0.009$, *$P<0.0007$; Mann Whitney U-test.

FIG. 15A depicts tumor size in mice of indicated genotype and treatment. The number of mice in each group are, LKR13 injected BLT1⁺/⁺Rag2⁻/⁻ (n=12); LKR13 with CS injected BLT1⁺/⁺Rag2⁻/⁻ (n=10); LKR13 injected BLT1⁻/⁻Rag2⁻/⁻ (n=6); LKR13 with CS injected BLT1⁻/⁻Rag2⁻/⁻ (n=7).

FIG. 15B depicts Kaplan-Meier survival curves of tumor bearing mice. Data represent 8 mice per group; * (black) indicates comparison between LKR13 and LKR13 with CS injected BLT1⁺/⁺Rag2⁻/⁻ groups;  (red) indicates comparison between LKR13 with CS injected BLT1⁺/⁺Rag2⁻/⁻ and BLT1⁻/⁻Rag2⁻/⁻ groups.

FIG. 15C depicts representative images of tumors sixteen days post implantation for the indicated genotype and treatment; scale bars, 1 cm.

FIG. 15D depicts tumor weights at day 16 of LKR13 injected BLT1⁺/⁺Rag2⁻/⁻ (n=4); LKR13 with CS injected BLT1⁺/⁺Rag2⁻/⁻ (n=6); LKR13 injected BLT1⁻/⁻Rag2⁻/⁻ (n=5); LKR13 with CS injected BLT1⁻/⁻Rag2⁻/⁻ (n=7).

FIG. 15E depicts deposited CS particles in tumor sections viewed under polarized light; scale bars, 100 μm; insets show CS particles at higher magnification.

FIG. 15F depicts neutrophils, macrophages and mast cells expressed as percent of total tumor infiltrating immune cells identified by flow cytometry.

FIG. 15G depicts $LTB_4$ levels measured in tumor homogenates.

FIG. 15H depicts quantitative real-time PCR analysis of total tumor RNA showing fold increase of neutrophil-active chemokines; fold change over $BLT1^{+/+}Rag2^{-/-}$ injected with LKR13 cells.

Figure 16:
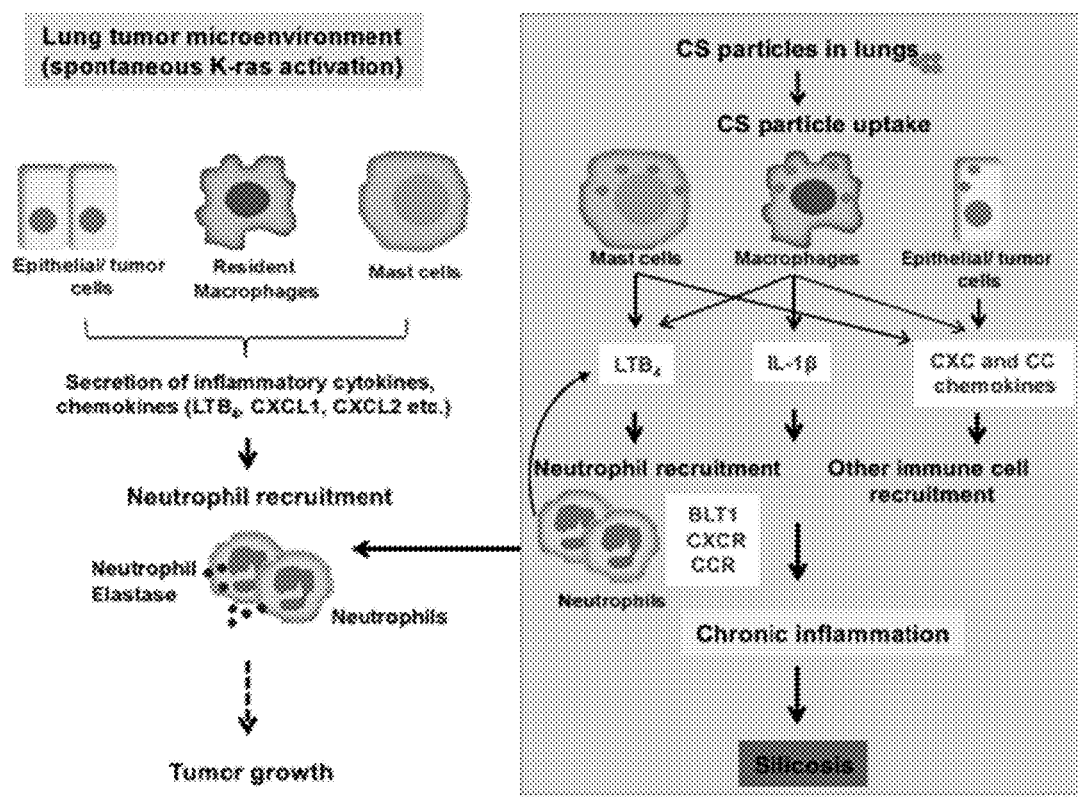

FIG. 16 shows a schematic model for the role of $LTB_4$-BLT1 axis in CS accelerated lung tumor growth. Spontaneous activation of K-ras gene in the lungs induces an inflammatory microenvironment (intrinsic pathway) that promotes cancer-related inflammation and tumor growth. This study shows that exposure to crystalline silica particles induces chronic inflammation (extrinsic pathway) which likely accelerates lung tumor growth. $LTB_4$ produced by mast cells and IL1β, $LTB_4$, CXC/CC chemokines by macrophages and CXC/CC chemokines by lung epithelial cells in response to CS exposure leads to sustained neutrophil accumulation. $LTB_4$/BLT1 axis sets the pace of CS induced sterile inflammation thereby promoting lung tumor progression.

Figure 17:
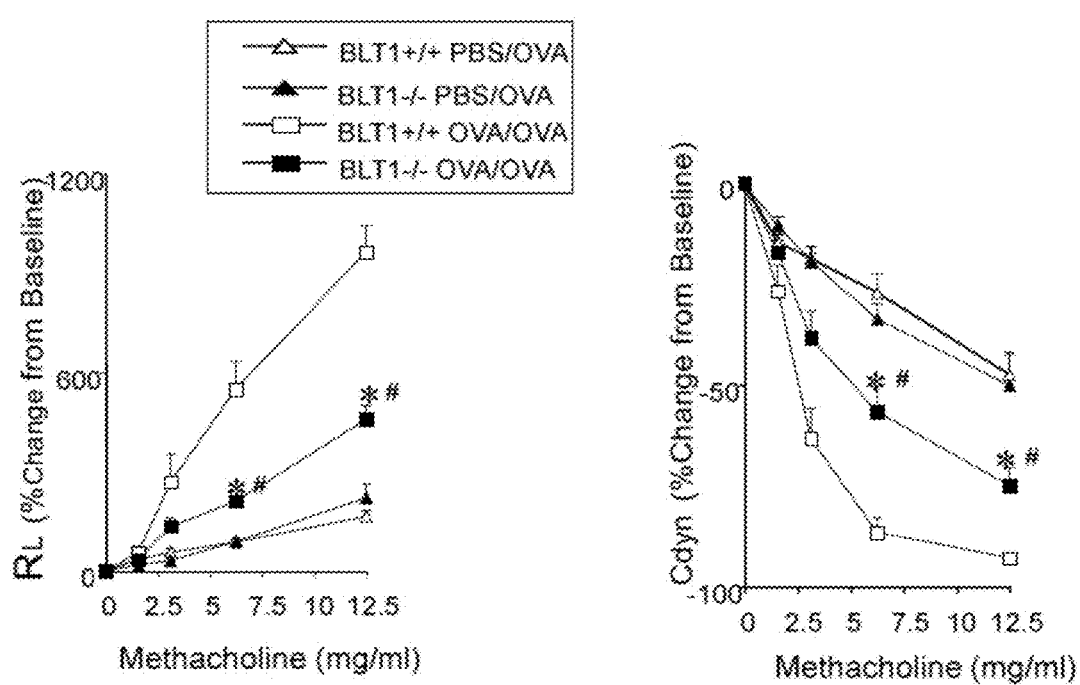

FIG. 17 shows pulmonary resistance ($R_L$) and dynamic compliance (Cdyn) of $BLT1^{+/+}PBS/OVA$, $BLT1^{-/-}PBS/OVA$, $BLT1^{+/+}OVA/OVA$, and $BLT1^{-/-}OVA/OVA$ groups at the indicated methacholine concentrations.

Figure 18A:
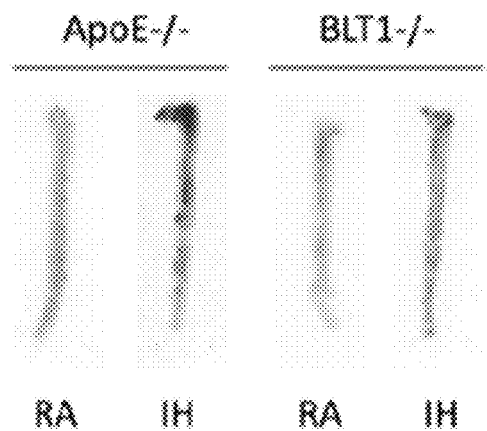
Figure 18B:
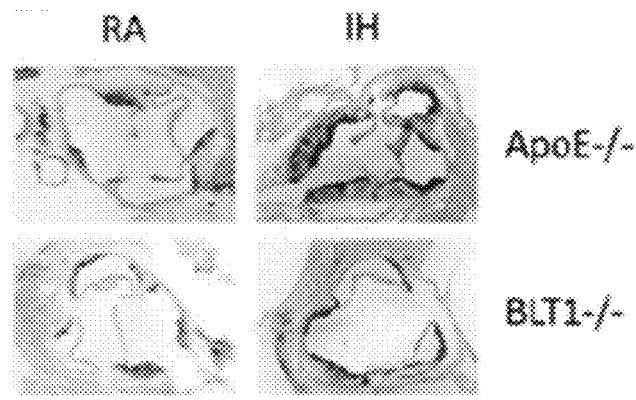
Figure 18C:
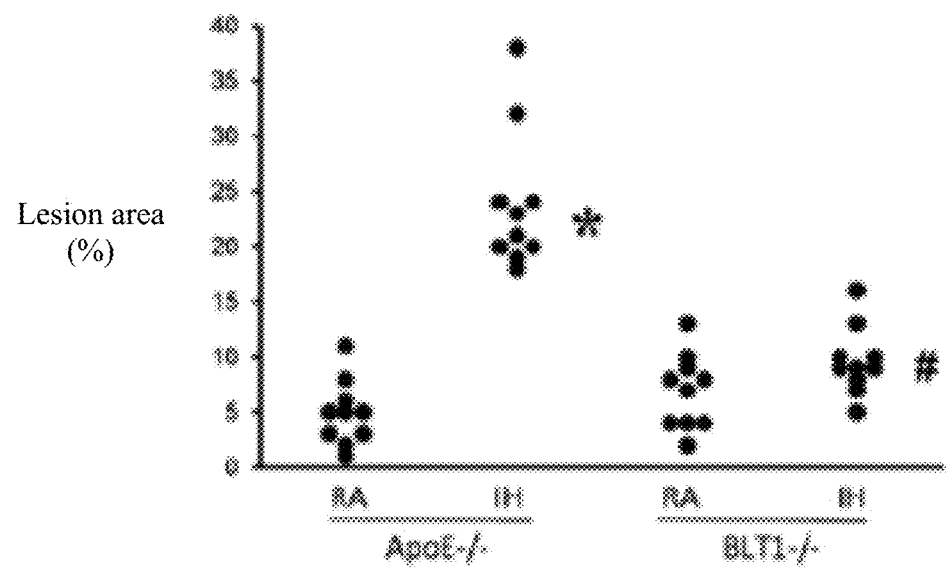

FIGS. 18A-C show that sleep apnea induced atherosclerosis is BLT1 dependent.

FIG. 18A depicts the changes in $ApoE^{-/-}$ and $BLT1^{-/-}$ groups exposed to room air (RA) and intermittent hypoxia (IH).

FIG. 18B depicts lesions formed in $ApoE^{-/-}$ and $BLT1^{-/-}$ groups exposed to room air (RA) and intermittent hypoxia (IH).

FIG. 18C depicts lesion area in $ApoE^{-/-}$ and $BLT1^{-/-}$ groups exposed to room air (RA) and intermittent hypoxia (IH).

Figure 19:
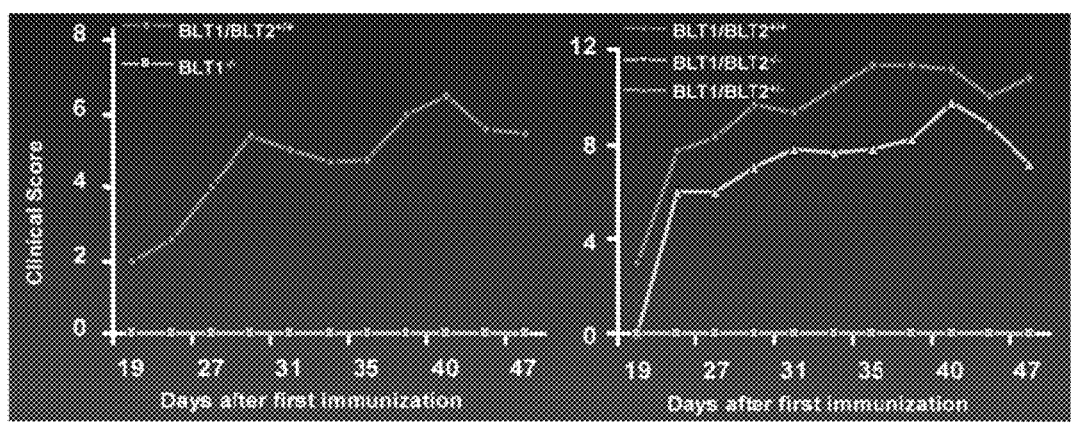

FIG. 19 shows inflammation in $BLT1/BLT2^{+/+}$, $BLT1/BLT2^{-/-}$, $BLT1/BLT2^{+/-}$, and $BLT1^{-/-}$ groups at the indicated time after first immunization.

Figure 20:
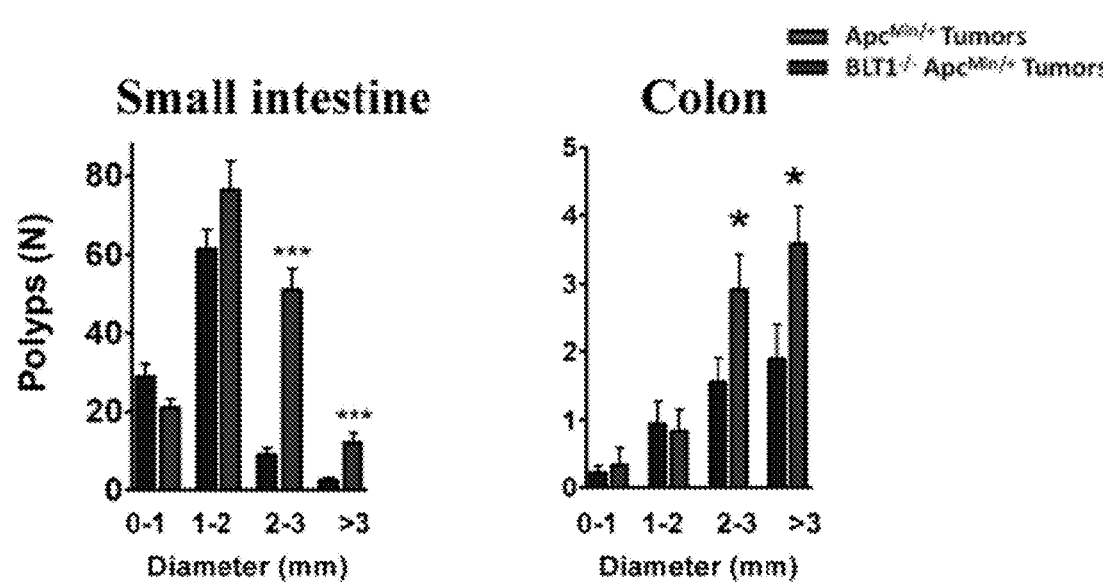

FIG. 20 shows the number and size of polyps formed in the small intestine and colon of $Apc^{Min/+}$ and $BLT1^{-/-}Apc^{Min/+}$ mice. This study showed increased tumor size in $BLT1^{-/-}Apc^{Min/+}$ mice.

Figure 21A:
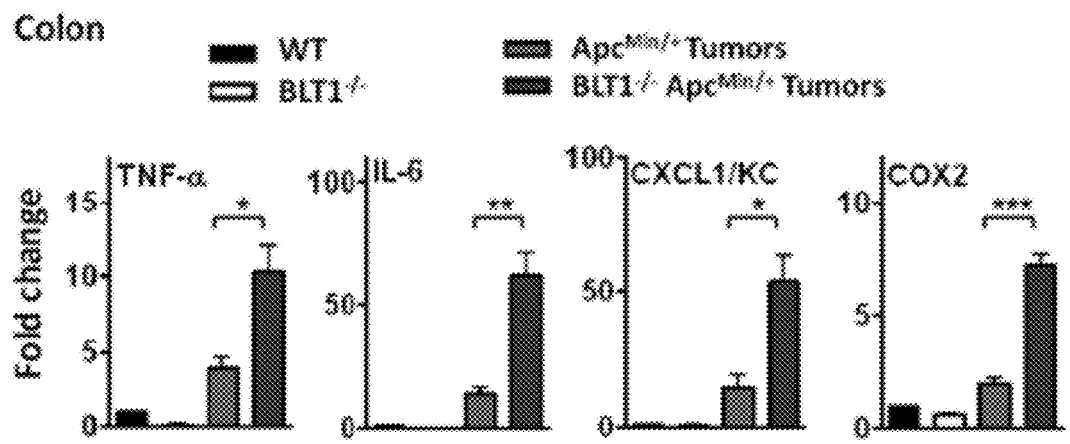
Figure 21B:
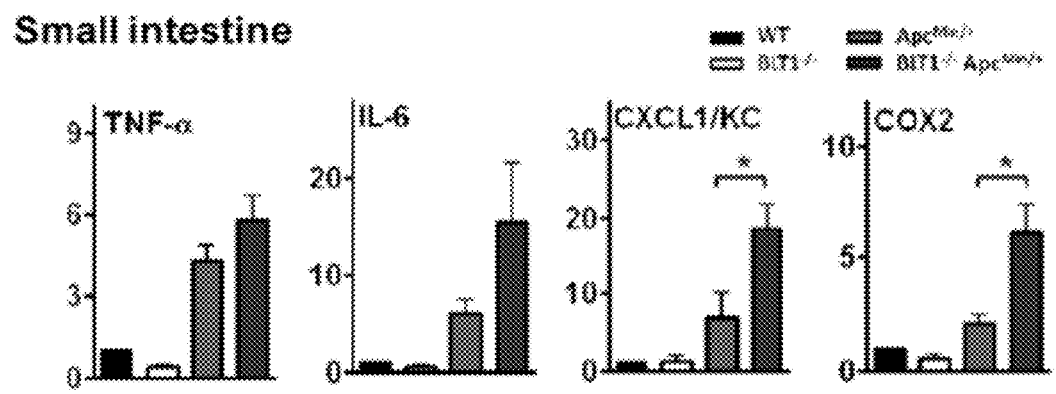

FIGS. 21A-B show fold change in wild type (WT), $BLT1^{-/-}$, $Apc^{Min/+}$ tumor, and $BLT1^{-/-} Apc^{Min/+}$ tumor groups exposed to TNF-α, IL-6, CXCL1/KC, and COX2. This study showed increased inflammation in tumors of $BLT1^{-/-}Apc^{Min/+}$ mice.

FIG. 21A shows fold change in the colon.

FIG. 21B shows fold change in the small intestine.

Figure 22:
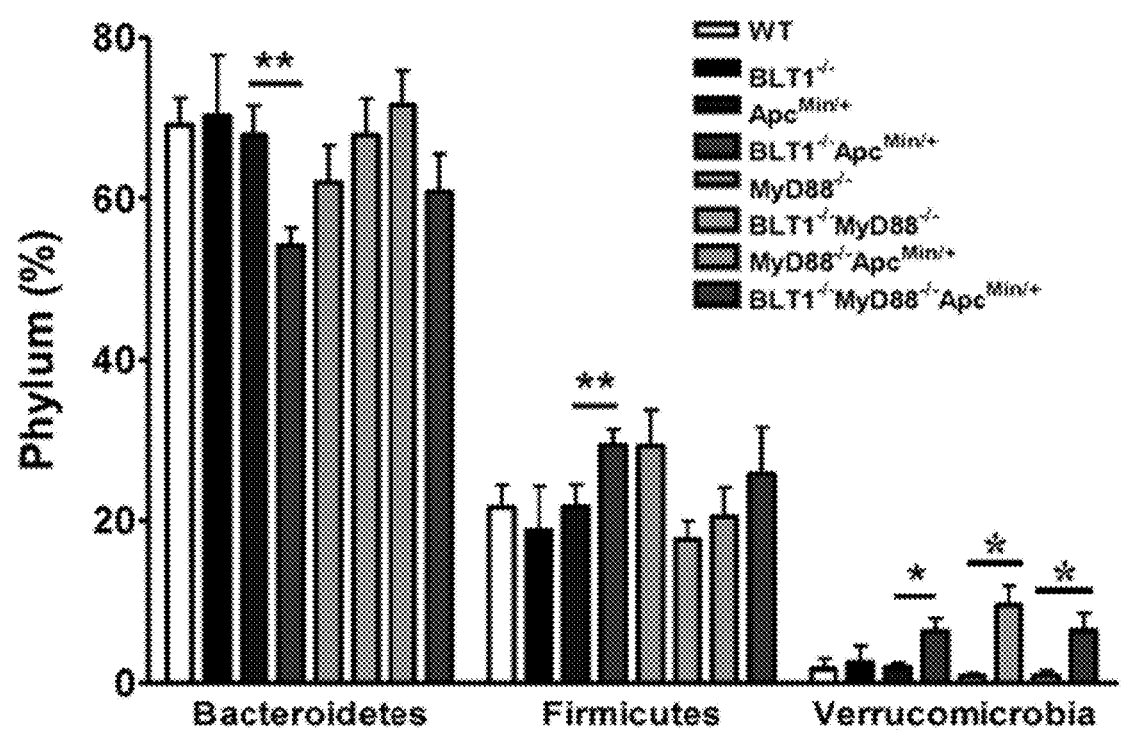

FIG. 22 shows an analysis of gut microbiota in various groups of colon cancer mice. The various groups include wild type (WT), $BLT1^{-/-}$, $Apc^{Min/+}$, $BLT1^{-/-}Apc^{Min/+}$, $MyD88^{-/-}$, $BLT1^{-/-}MyD88^{-/-}$, $MyD88^{-/-}Apc^{Min/+}$, and $BLT1^{-/-}MyD88^{-/-}Apc^{Min/+}$.

Figure 23:
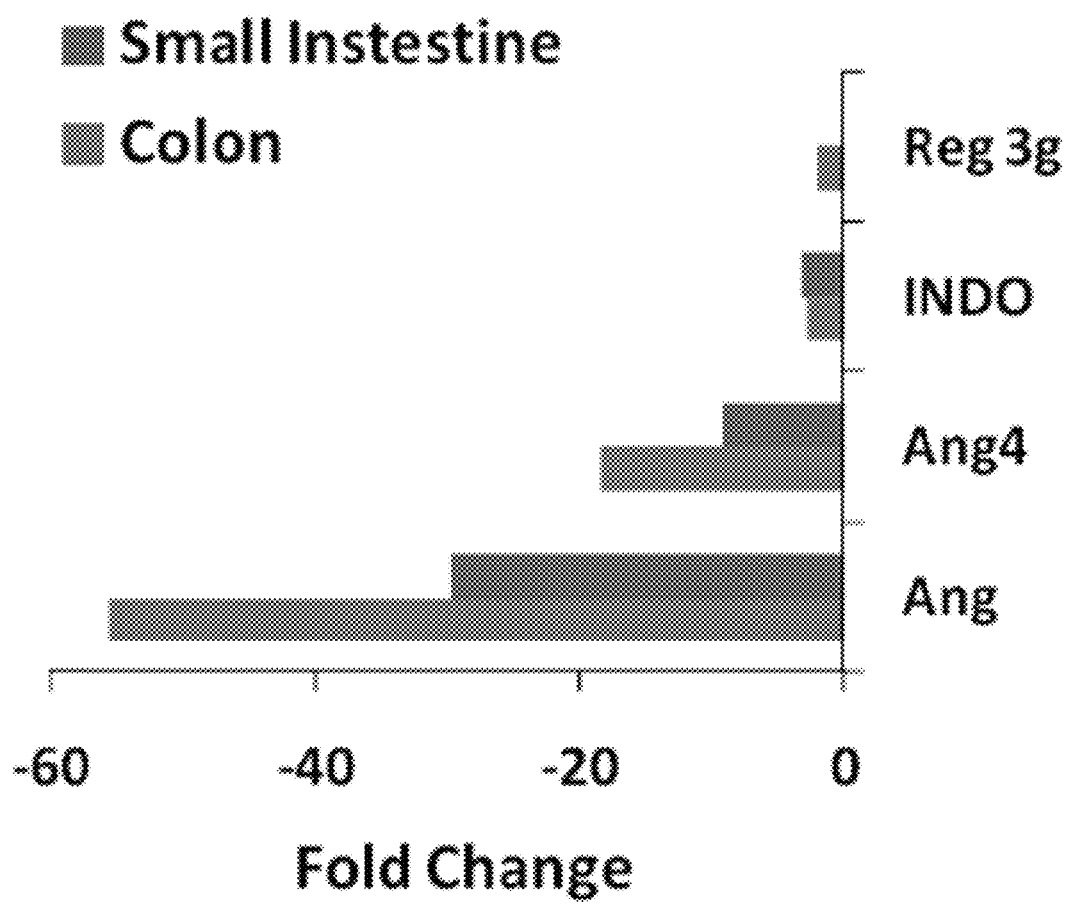

FIG. 23 shows fold change in small intestine and colon groups exposed to Reg3g, INDO, Ang4, and Ang. This study showed that expression of bactericidal proteins is down regulated in $BLT1^{-/-}Apc^{Min/+}$ tumors.

Figure 24:
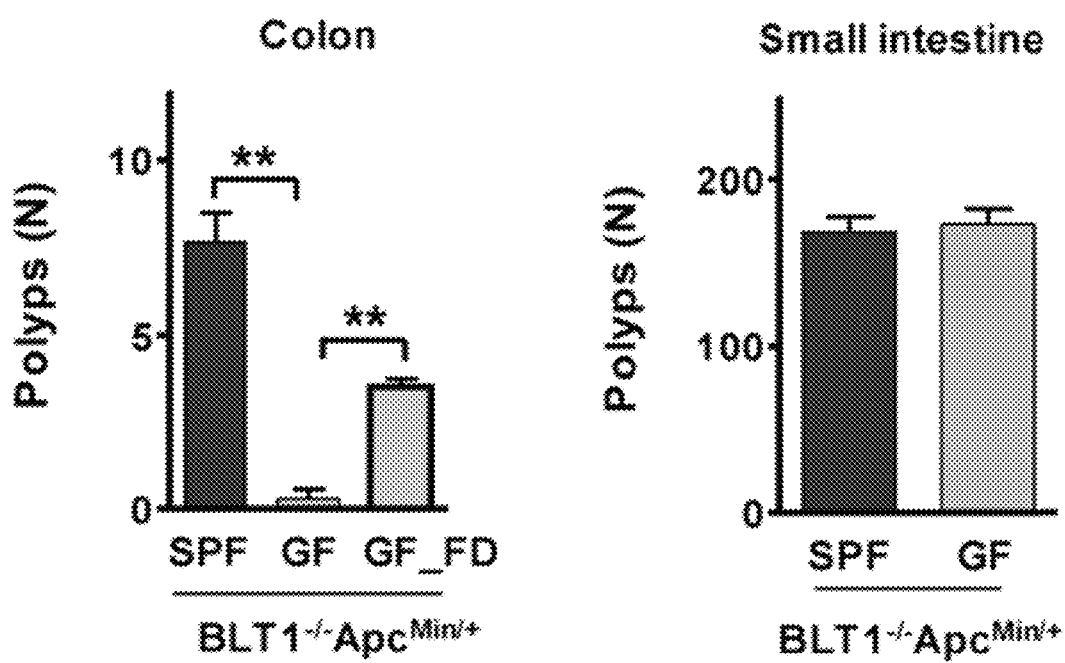

FIG. 24 shows the number of polyps in the colon and small intestine of specific pathogen free (SPF), germ free (GF), and germ free defined flora (GF_FD) groups of $BLT1^{-/-}Apc^{Min/+}$ mice. This study showed that germ free $BLT1^{-/-} Apc^{Min/+}$ mice are free of colon cancer.

FIGS. 25A-D show glucose levels of wild type (WT) and $BLT1^{-/-}$ mice at the indicated times. This study showed that BLT1 mediated inflammation promotes insulin resistance during diet induced obesity.

Figure 25A:
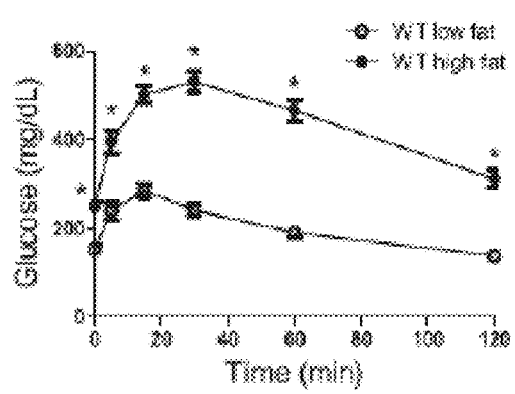

FIG. 25A depicts glucose concentrations (mg/dL) of low fat and high fat wild type (WT) mice at the indicated times.

Figure 25B:
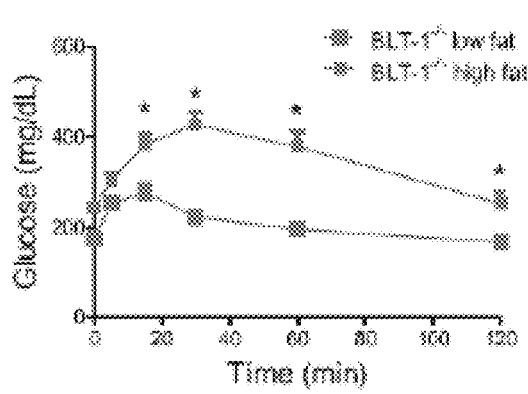

FIG. 25B depicts glucose concentrations (mg/dL) of low fat and high fat $BLT1^{-/-}$ mice at the indicated times.

Figure 25C:
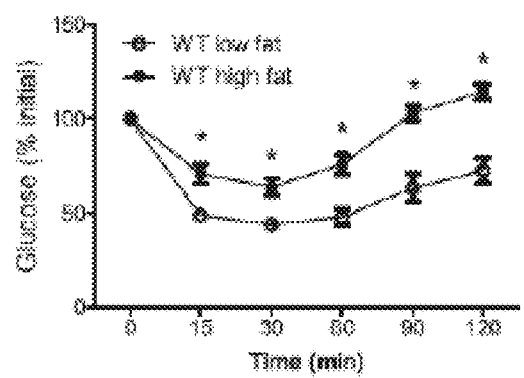

FIG. 25C depicts glucose percentage of low fat and high fat wild type (WT) mice at the indicated times.

Figure 25D:
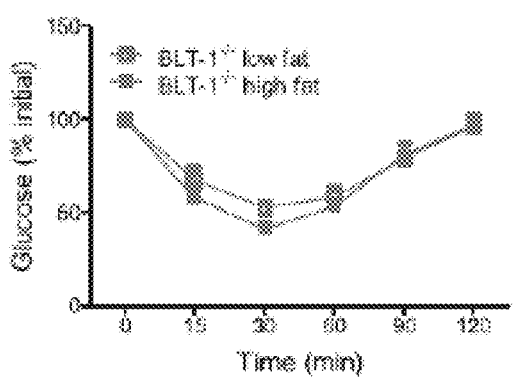

FIG. 25D depicts glucose percentage of low fat and high fat $BLT1^{-/-}$ mice at the indicated times.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Although any methods, devices, and materials similar or equivalent to those described herein can be used in the practice or testing of the presently-disclosed subject matter, representative methods, devices, and materials are now described.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes compositions and methods for use in treating silicosis, lung cancer, and/or a lung inflammatory disorder.

Compositions disclosed herein include pharmaceutical compositions comprising a BLT1 inhibitor and a pharmaceutically-acceptable carrier.

Methods disclosed herein comprise administering an effective amount of a BLT1 inhibitor, or a composition comprising a BLT1 inhibitor, to a subject in need thereof.

The terms "treatment" or "treating" refer to the medical management of a subject with the intent to cure, ameliorate, stabilize, or prevent a condition or disorder (e.g., silicosis, lung cancer, lung inflammatory disorder). This term includes active treatment, that is, treatment directed specifically toward the improvement of a condition, and also includes causal treatment, that is, treatment directed toward removal of the cause of the associated condition. In addition, this term includes palliative treatment, that is, treatment designed for the relief of symptoms rather than the curing of the condition; preventative treatment, that is, treatment directed to minimizing or partially or completely inhibiting the development of symptoms or disorders of the associated condition; and supportive treatment, that is, treatment employed to supplement another specific therapy directed toward the improvement of the associated disease, pathological condition, or disorder.

With regard to administering the compound, the term "administering" refers to any method of providing inhibitor and/or pharmaceutical composition thereof to a subject. Such methods are well known to those skilled in the art and include, but are not limited to, oral administration, intravenous administration, intra-arterial administration, intramuscular administration, subcutaneous administration, intravitreous administration, including via intravitreous sustained drug delivery device. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The terms "subject" or "subject in need thereof" refer to a target of administration, which optionally displays symptoms related to a particular disease, condition, disorder, or the like. The term "subject" does not denote a particular age or sex. Thus, adult and newborn subjects, whether male or female, are intended to be covered. The term "subject" includes human and veterinary subjects.

As will be recognized by one of ordinary skill in the art, the terms "suppression," "suppressing," "suppressor," "inhibition," "inhibiting" or "inhibitor" do not refer to a complete elimination of activity in all cases. Rather, the skilled artisan will understand that the term "suppressing" or "inhibiting" refers to a reduction or decrease. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some exemplary embodiments the presently-disclosed subject matter includes use of a BLT1 inhibitor that is a small molecule, a polypeptide or an siRNA molecule. In some exemplary embodiments the presently-disclosed subject matter includes use of a BLT1 inhibitor that is a BLT1 receptor antagonist. In some exemplary embodiments the presently-disclosed subject matter includes use of a BLT1 inhibitor as disclosed in Hicks, A., et al., *Leukotriene B4 receptor antagonists as therapeutics for inflammatory disease: preclinical and clinical development*. Expert Opin.

Investig. Drugs, 2007. 16 (12): p. 1909-1920, which is incorporated herein by this reference.

As described herein, the presently-disclosed subject matter further includes pharmaceutical compositions comprising the compounds described herein together with a pharmaceutically acceptable carrier.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

The presently-disclosed subject matter further includes a kit that can include a compound or pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

The presently-disclosed subject matter is further illustrated by the following specific but non-limiting examples. The following examples may include compilations of data that are representative of data gathered at various times during the course of development and experimentation related to the present invention. Although any methods, devices, and materials similar or equivalent to those described herein can be used in the practice or testing of the presently-disclosed subject matter, representative methods, devices, and materials are now described.

EXAMPLES

Example 1

In the studies described in this Example, using the K-ras$^{LA1}$ mice that develop spontaneous lung tumors [21], the present inventors established a link between CS-induced chronic inflammation and lung tumor progression. CS exposure led to increased incidence of lung tumors and this process was attenuated in the absence of BLT1. The CS induced pulmonary inflammation and in particular, neutrophil recruitment was abrogated in BLT1$^{-/-}$ mice. Furthermore, CS exposure enhanced the growth of implantable lung tumors leading to reduced survival. Since neutrophils are known to promote lung cancer [22, 23], the present inventors investigated the cellular and molecular mechanisms involved in CS-mediated neutrophil recruitment to lungs. The results suggest an intricate interplay of mast cell, macrophage and epithelial cells derived lipid chemoattractant (LTB$_4$), cytokine (IL-1β) and neutrophil-active chemokines in coordinating CS-induced neutrophil migration. BLT1-mediated recruitment of neutrophils through mast cell produced LTB$_4$ appears to be the critical initial event in promoting CS-induced inflammation. Collectively, the present inventors' findings support targeting BLT1-mediated neutrophil recruitment for combating silicosis and associated lung cancer.

Results

Absence of BLT1 Abrogates the CS-Promoted Lung Tumor Growth

Figure 1A:
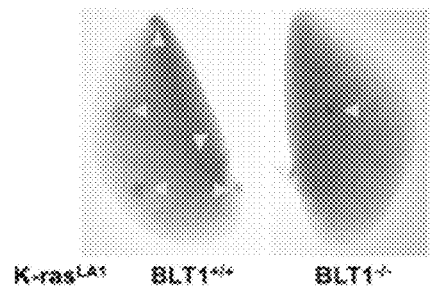
FIGS. 1A-C show reduced lung tumor incidence in the absence of BLT1. Lungs of untreated $BLT1^{+/+}K\text{-}ras^{LA1}$ and $BLT1^{-/-}K\text{-}ras^{LA1}$ mice at 105 days were analyzed for tumor multiplicity.
Figure 1B:
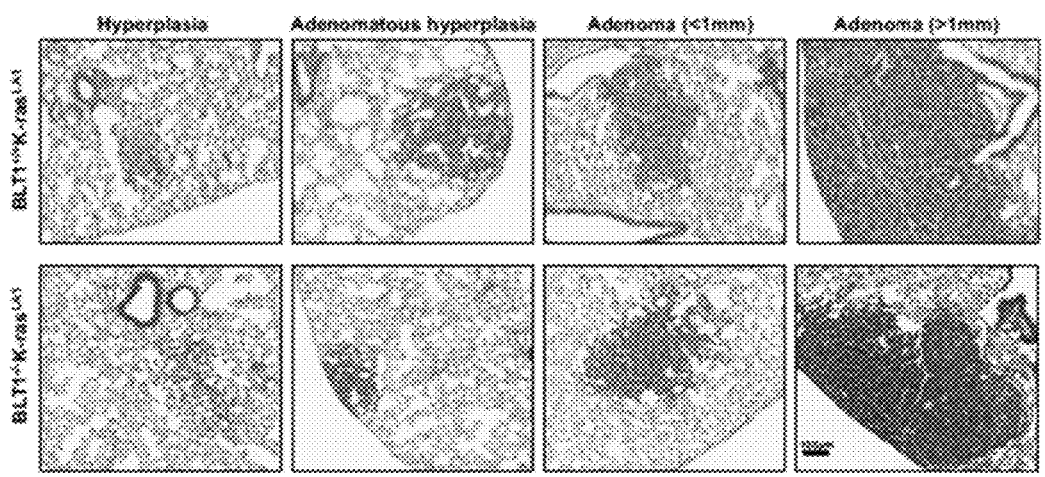
Figure 1C:
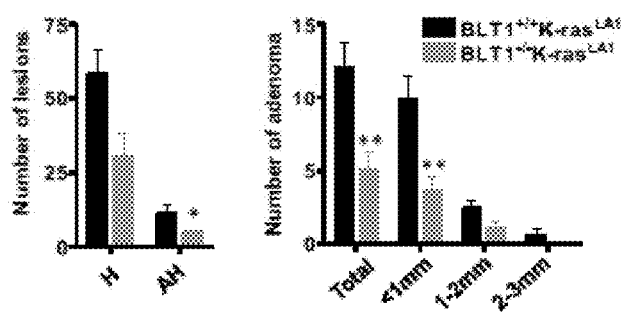

Spontaneous activation of K-ras induces an inflammatory microenvironment that promotes tumor growth [24]. To investigate the involvement of BLT1-mediated inflammation in spontaneous K-ras activation-induced lung tumor progression, the BLT1$^{-/-}$K-ras$^{LA1}$ mice were generated. As illustrated in FIGS. 1A-C, the K-ras$^{LA1}$ mice showed distinctly visible lung tumors at the age of 105 days whereas, the BLT1$^{-/-}$K-ras$^{LA1}$ mice showed fewer and smaller tumors (FIG. 1A). Detailed histopathological analysis of lungs performed after serial sectioning of the entire lungs at 200 μm intervals showed that both BLT1$^{+/+}$K-ras$^{LA1}$ and BLT1$^{-/-}$K-ras$^{LA1}$ mice developed similar lung lesions (FIG. 1B). However, the numbers of such lesions were significantly reduced in BLT1$^{-/-}$K-ras$^{LA1}$ mice (FIG. 1C).

To examine the effect of CS exposure on lung tumor growth K-ras$^{LA1}$ mice were instilled with CS. To determine the role of BLT1-mediated inflammation in this process, BLT1$^{-/-}$K-ras$^{LA1}$ mice were also exposed to CS. Equivalent exposure of CS in the lungs of both groups of mice was observed (FIGS. 2A-B) and tumors were scored in the histological sections. Following CS exposure, the BLT1$^{+/+}$K-ras$^{LA1}$ mice exhibited a significant increase in lung adenomas, the most common histological type found in 100% of each cohort (FIGS. 2C-D). In contrast, complete attenuation of increase in lung tumor incidence was observed in CS exposed BLT1$^{-/-}$K-ras$^{LA1}$ mice. These data suggests that CS exposure accelerates lung tumor growth through a process that requires BLT1.

BLT1 Controls CS-Induced Pulmonary Neutrophil Recruitment

Figure 4A:
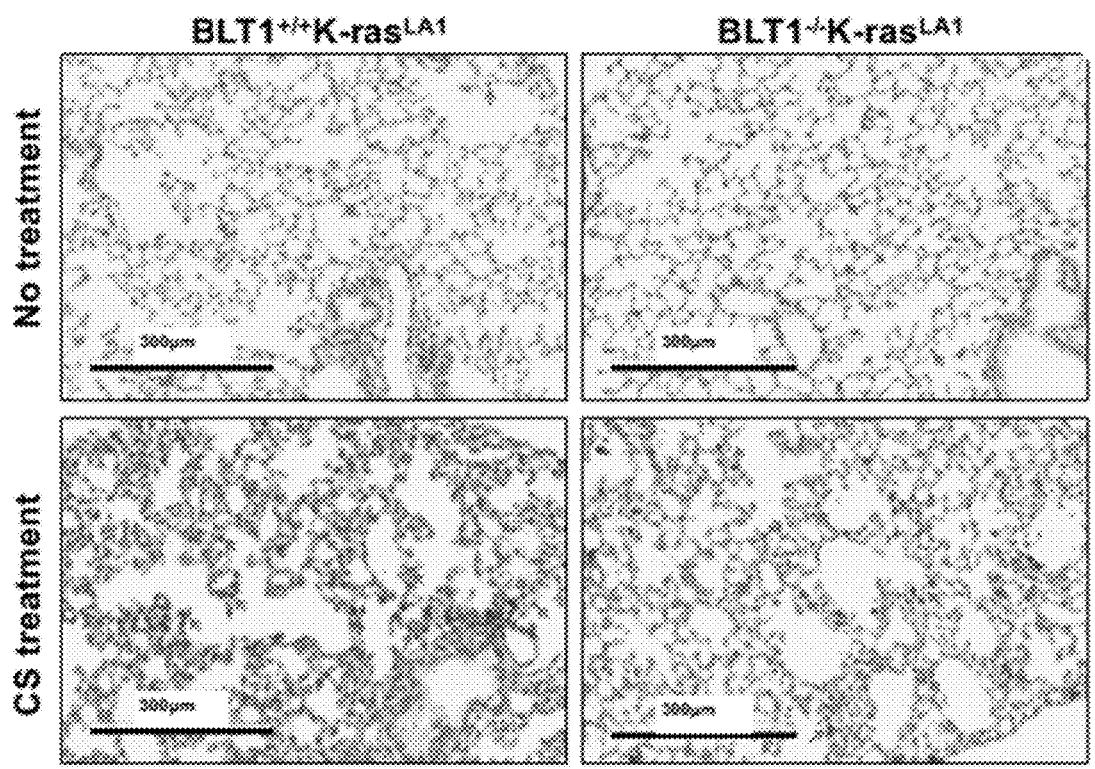
FIGS. 4A-B show similar macrophage influx into lungs of $BLT1^{+/+}K-ras^{LA1}$ and $BLT1^{-/-}K-ras^{LA1}$ mice post CS exposure. Lungs of $BLT1^{+/+}K-ras^{LA1}$ and $BLT1^{-/-}K-ras^{LA1}$ mice were analyzed for macrophage infiltration post 60 days of CS exposure.
Figure 4B:
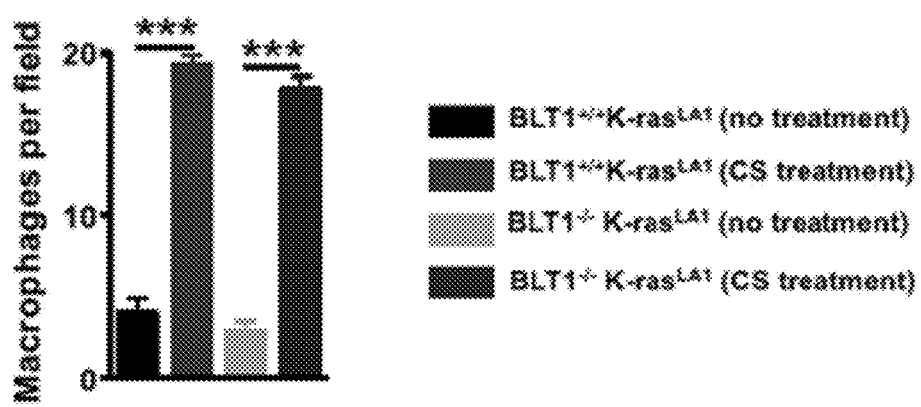

It is believed that CS-mediated increase in lung tumor incidence may be related to increased inflammation, an essential feature of silicosis. A close association of chronic inflammation and tumor promotion has been observed in various types of cancers [1, 25]. Therefore, the present inventors investigated the role of BLT1 in regulating CS-mediated chronic inflammation and thus controlling the pace of tumor growth. Histopathological examination of lung sections was carried out to assess inflammation. Features of acute silicosis including neutrophil aggregates, organizing pneumonia, type II pneumocyte proliferation, edema and fibroblastic proliferation as well as chronic inflammation features such as lymphocytic aggregates, expansion of interalveolar septa were all observed at 60 days post CS exposure in BLT1$^{+/+}$K-ras$^{LA1}$ mice (FIG. 3A). Although CS exposed BLT1$^{-/-}$K-ras$^{LA1}$ mice lungs also showed these histological features, the overall inflammation was significantly reduced in these mice (FIGS. 3A-B). In independent cohorts of CS-treated BLT1$^{+/+}$K-ras$^{LA1}$ mice, analysis of bronchoalveolar lavage fluids (BALF) 60 days post CS exposure by flow cytometry showed a significant increase in different leukocyte populations including neutrophils, macrophages and lymphocytes (FIG. 3C). Similar increases in macrophages and lymphocytes were also seen in CS exposed BLT1$^{-/-}$K-ras$^{LA1}$ mice but the neutrophil numbers were significantly lower compared to CS exposed BLT1$^{+/+}$K-ras$^{LA1}$ mice (FIG. 3C). Immunohistochemical analysis also showed similar levels of macrophage infiltration into lungs of both BLT1$^{+/+}$K-ras$^{LA1}$ and BLT1$^{-/-}$K-ras$^{LA1}$ mice (FIG. 4).

Since activated K-ras mutations are known to activate an intrinsic pathway of inflammation, the present inventors also analyzed CS-induced inflammation in BLT1$^{+/+}$ and BLT1$^{-/-}$ mice. Significant influx of leukocytes into the airways was observed in these mice (FIGS. 5A and 5C). In airways, neutrophil influx peaked very early at day 2, decreased by day 6 and again increased by day 30. However, neutrophil influx was significantly attenuated during the acute phase at day 2 and the chronic phase at day 30 in BLT1$^{-/-}$ mice (FIGS. 5B-C). In contrast, macrophage and lymphocyte influx was found to be similar in both BLT1$^{+/+}$ and BLT1$^{-/-}$ mice at 2, 6 or 30 days post CS exposure. To determine whether cellular distribution in the airways reflected changes in the total lungs, whole lung digests were analyzed by flow cytometry. At 2 days post CS exposure there was an increase in neutrophil influx in BLT1$^{+/+}$ mice that was significantly reduced in BLT1$^{-/-}$ mice (FIG. 5D).

Absence of BLT1 does not Impair CS-Induced Chemokine Production

Figure 6A:
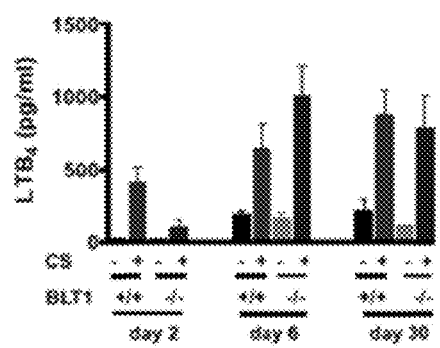
FIGS. 6A-D show that CS-induced neutrophil chemoattractants remain unaffected in the absence of BLT1. Mediators of CS-induced pulmonary inflammation were analyzed by assessing production of $LTB_4$ in whole lung lavage fluids (FIGS. 6A-B) and cytokines and chemokines in total lung RNA (FIGS. 6C-D).
Figure 6B:
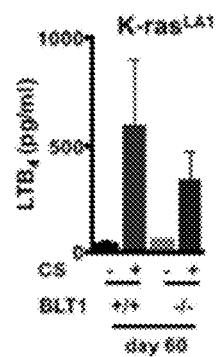

Since absence of BLT1 was found to attenuate neutrophil recruitment to lungs, the present inventors sought to analyze if deletion of BLT1 had an effect on the production of cytokines and chemokines involved in CS-induced neutrophilic inflammation. Levels of the BLT1 ligand LTB$_4$ were found to significantly increase in BAL fluids of BLT1$^{+/+}$ mice at 2, 6 or 30 days post CS exposure (FIG. 6A). A significant increase in LTB$_4$ was also observed in BLT1$^{+/+}$ K-ras$^{LA1}$ mice (FIG. 6B) 60 days post CS exposure. In BLT1$^{-/-}$ mice similar increase in LTB$_4$ levels was observed at all tested time points, with the exception of day 2 (FIGS. 6A-B).

Figure 6C:
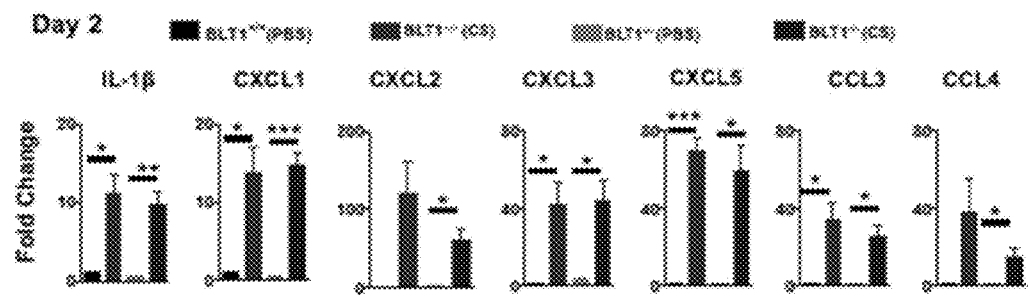
Figure 6D:
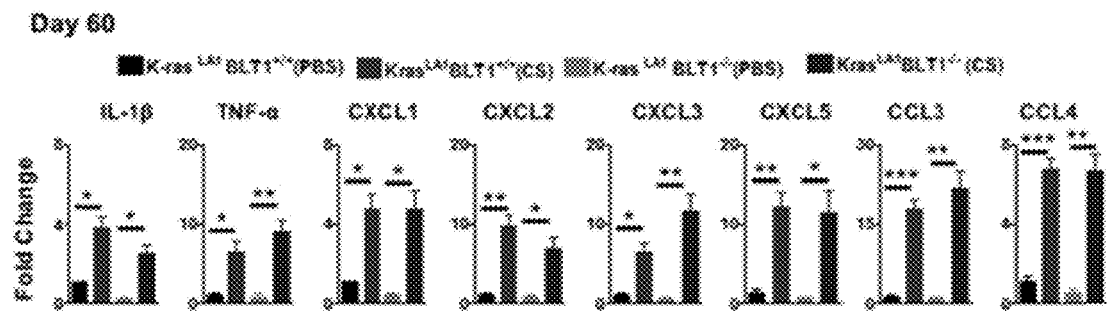
Figures 7A, 7B:
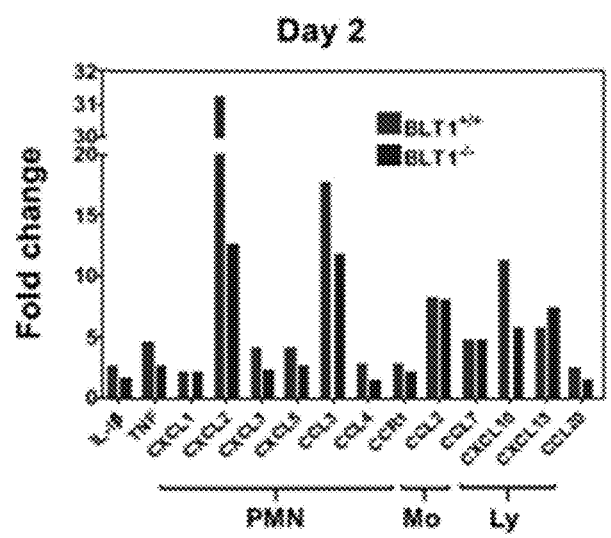
FIGS. 7A-B show microarray analysis for markers of CS-induced acute (day 2) and chronic (day 60) lung inflammation. Various cytokines, chemokines, and chemokine receptors; chemoattractants for neutrophils (PMN); monocytes (Mo); and lymphocytes (Ly) are indicated. Genes with a cut-off of ≥2 fold induction in mRNA over respective vehicle alone controls are shown; data represent pooled samples from 3 mice of each group.
Figure 8A:
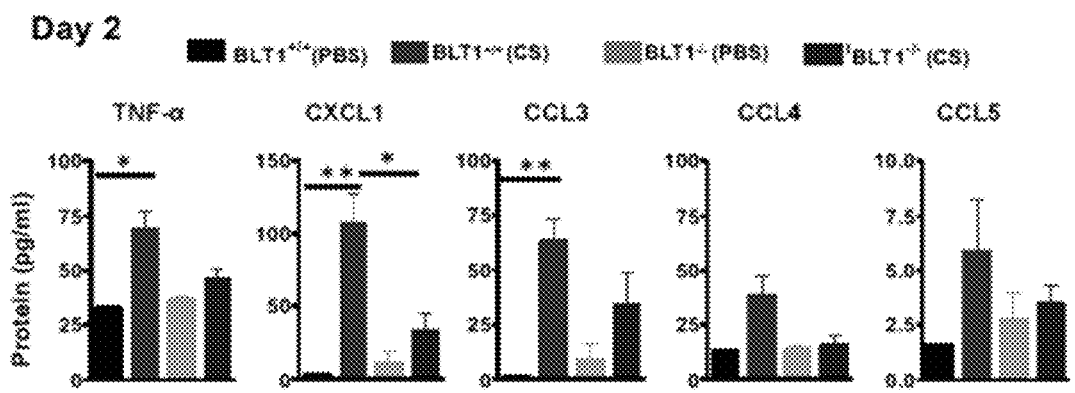
FIGS. 8A-B show multiplex analysis for markers of CS-induced inflammation. Whole lung lavage fluid was analyzed in multiplex assay. Error bars denote mean±SEM, *P<0.016, P<0.0035, *P<0.0002. Unpaired t-test.
Figure 8B:
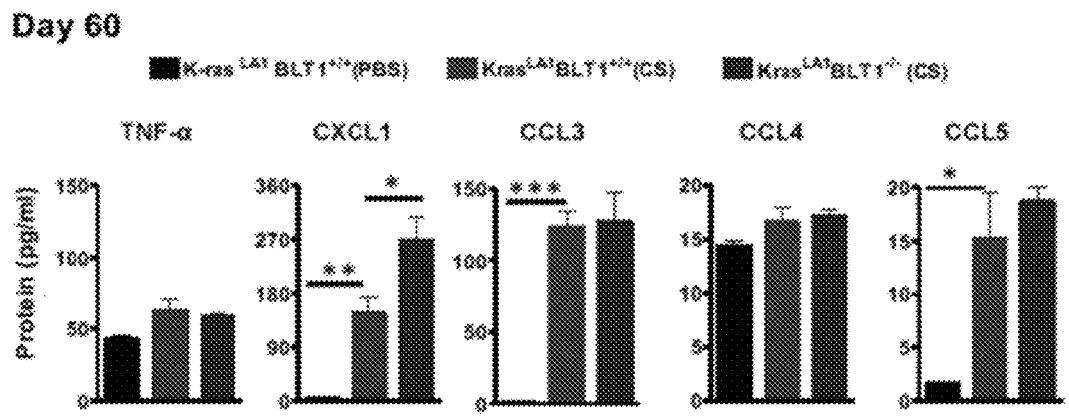

To determine global changes in CS-induced gene expression profiles total RNA isolated from lungs was analyzed by microarrays. The data analysis indicated that several markers and mediators of inflammation increased in BLT1$^{+/+}$ and BLT1$^{-/-}$ mice at 2 days post CS exposure as well as in BLT1$^{+/+}$K-ras$^{LA1}$ and BLT1$^{-/-}$K-ras$^{LA1}$ mice at 60 days post CS exposure. Of interest, inflammatory cytokines like IL-1β and TNF-α as well as number of chemokines and their receptors were upregulated upon CS exposure (FIG. 7). Real-time PCR analysis confirmed the CS-induced increase in neutrophil-active cytokines and chemokines both at early (day2) and late (day 60) times both in the presence and absence of BLT1 (FIGS. 6C-D). Multiplex analysis of neutrophil active chemokines in BAL fluids also showed significant increase upon CS exposure both in the presence and absence of BLT1 (FIG. 8). This suggests that neutrophil-active cytokines and chemokines may be produced in the absence of BLT1 signaling and yet are not sufficient to overcome attenuation of neutrophil influx in BLT1$^{-/-}$ lungs.

Cellular Mediators of CS-Induced Inflammation

In inflamed lungs neutrophil-active cytokines and chemokines may be produced from lung resident cells or recruited leukocytes. The present inventors next analyzed the CS-induced production of LTB$_4$, IL-1β and neutrophil-active chemokines in vitro by the lung adenocarcinoma cell line derived from K-ras$^{LA1}$ mice-LKR13 [24] and various murine primary cells including macrophages, neutrophils, mast cells and splenocytes. Among the primary cells macrophages and neutrophils but not splenocytes produced LTB$_4$ upon CS exposure (FIG. 9A). Bone-marrow derived mast cells produced the highest levels of CS-induced LTB$_4$ in a dose-dependent manner that peaked by 3 hours (FIGS. 9A and 10A-B). CS activated murine macrophages produced IL-1β, whereas mast cells and splenocytes did not secrete IL-1β (FIG. 9B). Primary macrophages and mast cells isolated from murine lungs were also tested for their ability to produce $LTB_4$ and IL-1β. CS activation of alveolar macrophages led to production of both $LTB_4$ and IL-1β whereas, lung mast cells produced $LTB_4$ but not IL-1β post CS exposure (FIGS. 9C-D).

The $LTB_4$ production by CS activation in the macrophage cell-line RAW264.7 was completely blocked by 5-lipoxygenase (5-LO) inhibitor, Zileuton (FIGS. 11A-C). The CS-induced $LTB_4$ was biologically active as determined by chemotaxis of 300.19 cells expressing BLT1 as well as $BLT1^{+/+}$ neutrophils but not the parental 300.19 cells or $BLT1^{-/-}$ neutrophils (FIGS. 11D-E).

Independent Regulation of CS-Induced $LTB_4$ and IL1-β Production

Since both $LTB_4$ and IL-1β appear to be critical for silicosis, the inter-dependence of their production was analyzed. CS exposed mast cells from inflammasome pathway-deficient ($NALP3^{-/-}$, $ASC^{-/-}$, $IL-1\alpha\beta^{-/-}$) or IL-1 response deficient ($IL-1R^{-/-}$, $MyD88^{-/-}$) as well as $BLT1^{-/-}$ mice secreted $LTB_4$, but not the $5-LO^{-/-}$ mast cells (FIG. 12A). As expected, CS treated macrophages from inflammasome pathway-deficient ($NALP3^{-/-}$, $ASC^{-/-}$, $IL-1\alpha\beta^{-/-}$) mice did not secrete IL-1β, while macrophages from 5-LO pathway deficient ($BLT1^{-/-}$ or $5-LO^{-/-}$) mice were found to secrete IL-1β similar to wild-type macrophages (FIG. 12B). These data suggest that CS-induced activation of 5-LO and the inflammasome pathway are completely independent of each other and absence of BLT1 does not affect either of the pathways.

Although LKR13 cells did not secrete $LTB_4$ or IL-1β (FIGS. 9A-B), they produced neutrophil-active chemokines CXCL1, CXCL2, CXCL3, CXCL5 and CCL5 in response to CS stimulation, suggesting that pathways leading to the production of these chemokines are most likely independent of 5-LO or inflammasome activation (FIG. 13). Many of these chemokines were also produced by both $BLT1^{+/+}$ and $BLT1^{-/-}$ macrophages and mast cells (FIG. 13).

CS-Induced Inflammation in Air Pouch Model Requires $LTB_4$/BLT1 Axis

The in vitro studies showed that mast cells are a major source of $LTB_4$ production and the absence of BLT1 clearly reduced lung inflammation and neutrophil influx in vivo. Previous studies have shown that CS mediated lung inflammation is dependent on the presence of mast cells [26]. The present inventors adopted the murine air-pouch model [27] to assess the contribution of mast cells and the role of $LTB_4$-BLT1 axis in neutrophil recruitment during CS-induced inflammation. In this model, CS exposure of $BLT1^{+/+}$ mice induced the production of $LTB_4$ (FIG. 14A) accompanied by influx of neutrophils (FIGS. 14B-C). This response however was significantly dampened in the $BLT1^{-/-}$ as well as in mast cell deficient mice (FIGS. 14A-C). These data shows that neutrophil recruitment is an early event during CS exposure and is controlled by mast cell-mediated $LTB_4$ production and expression of BLT1 on neutrophils.

CS-Induced Inflammation Promotes Growth of Implanted Lung Tumors

To determine if CS accelerates the growth of implanted lung tumors, the present inventors adopted LKR13 s.c. tumor model. LKR-13 cells mixed with CS-particles in matrigel were implanted subcutaneously into $Rag2^{-/-}$ mice. In $BLT1^{+/+}Rag2^{-/-}$ mice, CS exposure led to a significant increase in tumor growth and consequently reduced their survival (FIGS. 15A-D). Interestingly, the $BLT1^{-/-}Rag2^{-/-}$ mice displayed reduced tumor growth and survival advantage (FIGS. 15A-D). Analysis of immune cell infiltration in these tumors showed that presence of CS resulted in increased neutrophil influx whereas macrophages and mast cells remained unchanged in $BLT1^{+/+}Rag2^{-/-}$ mice (FIG. 15E). In tumors growing in $BLT1^{-/-}Rag2^{-/-}$ mice neutrophil influx was significantly reduced compared to $BLT1^{+/+}Rag2^{-/-}$ mice whereas the macrophage and mast cell numbers were unchanged. Analysis of neutrophil-active chemokines indicated significant attenuation in the levels of $LTB_4$, CXCL1 and CCL3 in $BLT1^{-/-}$ mice post CS exposure (FIGS. 15E-F). These results emphasize a direct role for CS in promoting lung tumor growth that is dependent on $LTB_4$/BLT1-mediated inflammation.

DISCUSSION

Exposure to CS has long been associated with increased susceptibility to lung cancer in humans [8]. The results presented here show that CS promotes tumor progression in well-defined spontaneous and implantable mouse lung tumor models. The data suggests that complex interplay of cellular and molecular mediators orchestrate CS-mediated lung inflammation. Mast cells and macrophages produce $LTB_4$ and IL-1β upon CS exposure leading to sustained neutrophilic inflammation that is further maintained by the chemokines produced by the lung epithelial cells (FIG. 16). This chronic inflammatory micro-environment promotes lung tumor progression.

Lung tumor progression is associated with activation of both intrinsic and extrinsic pathways of inflammation [1, 2, 7]. Transforming mutations in the K-ras oncogene found in ~30% of human lung adenocarcinomas activate the intrinsic pathway of inflammation by activating NF-kB and consequent production of cytokines and chemokines [28]. Inflammation initiated by extrinsic factors such as exposure to CS may also promote cigarette smoke carcinogen induced tumor progression [8]. While CS has been designated as a human carcinogen by IARC (International Agency for Research on Cancer) [8], the causal relationship of CS exposure and lung cancer progression remained unclear due to lack of experimental model systems. Recent studies have shown that NNK-initiated lung tumor incidence is increased upon CS exposure [29]. In this study, the present inventors provide evidence that CS exposure accelerates lung tumor growth in a spontaneous K-ras$^{LA1}$ mouse model (FIG. 2) and this enhancement is dependent on BLT1-mediated chronic inflammation (FIG. 3). Furthermore, the s.c implantable lung tumor model provided direct evidence for the tumor promoting effects of CS (FIG. 15). Co-implantation of K-ras mutated lung tumor cells with CS resulted in accelerated tumor growth that reduced the survival of tumor bearing mice. In this model also absence of BLT1 reduced the tumor burden and improved survival, suggesting that BLT1 mediated inflammation is a crucial component in CS-induced tumor promotion.

CS exposure is known to induce cell death [30] leading to the recruitment and activation of a variety of leukocytes including mast cells, macrophages and neutrophils. The data herein outlines the cellular and molecular basis for CS-induced inflammation (FIG. 16). Mast cells are known to be essential for the full development of CS-induced lung inflammation and silicosis [31]. Studies presented here with cultured mast cells showed that CS exposure leads to significantly more $LTB_4$ production by mast cells relative to other myeloid cells suggesting that mast cell activation is likely an important step in CS-induced inflammation (FIG. 9). This was further substantiated by the observation of attenuated $LTB_4$ levels and neutrophils in the CS-exposed air pouch of mast cell deficient mice (FIG. 14). Mast cell produced $LTB_4$ along with macrophage secreted $LTB_4$ and IL-1β, coordinate with the epithelial cell generated chemokines to orchestrate neutrophil migration into inflamed lungs. Although CS exposure also leads to lymphocytic infiltration into lungs, it is known that innate immune processes are sufficient to drive silicosis in the absence of lymphocytes [32]. Consistent with this finding, splenocytes did not produce $LTB_4$ or IL-1β in response to CS activation (FIGS. 9A-B).

Earlier studies have shown that various cytokines and chemokines such as IL-β, TNF-α, TGF-β, IL-6, IL-8, IL-17A, CCL2 and CCL3 mediate silicosis [33-37]. Among these mediators, production of IL-1β through inflammasome activation appears to be most critical for CS-induced lung inflammation [36, 38-40]. The present inventors' study shows that production of $LTB_4$ is also critical for CS-induced lung inflammation (FIGS. 6A-B). However, in CS exposed lungs absence of BLT1 did not influence production of mediators including IL-1β at early or late times in presence or absence of an activating K-ras mutation in vivo (FIG. 6). Similarly, BLT1 deficiency also did not impact the production of IL-1β or neutrophil-active chemokines by CS exposed cells in vitro (FIGS. 12B and 13). Moreover, CS-exposure of the inflammasome pathway deficient or IL-1 deficient mast cells did not impact the $LTB_4$ production (FIG. 12A). Thus, CS activates parallel pathways for the production of IL-1β and $LTB_4$. Although neutrophil recruitment was significantly compromised in the absence of BLT1, it was not completely attenuated (FIGS. 3C, 5C, 14C, and 15C) possibly due to the production of IL-1β and CC/CXC neutrophil chemokines.

In various inflammatory diseases, relay of molecules that orchestrate recruitment of different cell types are of critical importance towards disease manifestation. In this regard, extremely coordinated tissue chemotaxis of neutrophils in mouse models of inflammatory arthritis [20] or sterile injury [41] were also shown to be initiated by $LTB_4$. In arthritis models $LTB_4$/BLT1 axis was critical for initial neutrophil recruitment into the joint leading to the sequential production of IL-1β and neutrophil active chemokine production that sustains joint inflammation. In contrast to these observations, current data shows that absence of BLT1 did not impair production of neutrophil-active cytokine and chemokines in the CS exposed lungs. A reduction in $LTB_4$ levels observed in air pouch of $BLT1^{-/-}$ mice were possibly due to impairment in recruitment of $LTB_4$ producing neutrophils (FIG. 14A). Together, these data suggests that CS exposed mast cells, macrophages and epithelial cells secrete lipids ($LTB_4$)-cytokines (IL-1β)-chemokines (CXCL, CCL) independently of each other that co-ordinate recruitment of neutrophils. However, $LTB_4$-BLT1 axis plays the most critical role such that absence of BLT1 significantly dampens this response.

Pro-tumorigenic activity of tumor-associated neutrophils is increasingly being appreciated in lung and other cancers [23, 42-45]. Inhibition of CXCR2-mediated neutrophil infiltration into lung tumors was shown to be associated with reduced tumor growth [23, 28, 46]. Neutrophil numbers within the tumor correlates to poor prognosis in NSCLC [47]. Interestingly, in NSCLC patients an increase of neutrophil chemoattractants $LTB_4$ and IL-8 in exhaled breath condensate were reported [48]. Again, levels of $LTB_4$ and IL-8 were found to increase with progression of NSCLC stages I through IV indicating the importance of $LTB_4$ and IL-8 in recruiting neutrophils into lung tumors. Thus, a common feature of lung cancer progression appears to be association of neutrophils in the tumor. The results presented here show a strong correlation between rapid tumor growth and increased neutrophilic inflammation both in spontaneous and implantable lung tumor models. Furthermore, neutrophil recruitment is dependent on BLT1 expression under different settings including the lungs of $Kras^{LA1}$ mice, skin air pouch and in the s.c. implantable tumor models suggesting a critical function for $LTB_4$/BLT1 axis in regulating CS-mediated inflammation. While the neutrophilic inflammation is most likely mediator of CS-promoted tumor progression, further studies are required to establish a direct cause and effect relationship in these models.

Methods:

Mice:

All mice were on C57BL/6 background and were sex and-age matched at 6-7 weeks. K-ras$^{LA1}$ mice was obtained from NCI mouse repository and subsequently crossed onto BLT1$^{-/-}$ background to generate BLT1$^{-/-}$K-ras$^{LA1}$ mice. Rag2$^{-/-}$ mice was obtained from Taconic (Germantown, N.Y.) and subsequently crossed onto BLT1$^{-/-}$ background to generate BLT1$^{-/-}$Rag2$^{-/-}$ mice. C57BL/6J (BLT1$^{+/+}$), Kit$^{W-sh/W-sh}$, MyD88$^{-/-}$ mice were purchased from Jackson Laboratories. BLT1$^{-/-}$ mice were described previously [49]. IL-1αβ$^{-/-}$ and 5-LO$^{-/-}$ mice were from Dr. A. Luster. IL-1R$^{-/-}$ mice were kindly provided by Dr. Jun Yan at the University of Louisville. Bone marrow from NALP3$^{-/-}$ and ASC$^{-/-}$ mice were provided by Dr. Kate Fitzgerald at the University of Massachusetts. All mice were maintained under specific pathogen-free conditions and all the procedures were approved by University of Louisville Institutional Animal Care and Use Committee.

CS Instillation in Mouse Lungs:

Crystalline silica (MIN-U-SIL-5; average particle diameter 1.7 μm) was obtained from U.S. Silica Co., WV and was made endotoxin-free by baking at 200° C. overnight. 45 days old BLT1$^{+/+}$, BLT1$^{-/-}$, BLT1$^{+/+}$K-ras$^{LA1}$ and BLT1$^{-/-}$K-ras$^{LA1}$ mice were either left untreated or surgically instilled (intra-tracheal) with endotoxin-free PBS (vehicle) or 2 mg of endotoxin-free crystalline silica suspended in vehicle without sonication. CS particle suspension was vortexed before instillation to avoid settling of the particles. Mice were treated with antibiotics for a week before surgery and were continuously maintained on antibiotics until euthanized. Lungs from BLT1$^{+/+}$K-ras$^{LA1}$ and BLT1$^{-/-}$K-ras$^{LA1}$ mice were analyzed 60 days after PBS or CS instillation and lungs from BLT1$^{+/+}$, BLT1$^{-/-}$ mice were analyzed after 2, 6 or 30 days after PBS or CS instillation as indicated.

CS-Induced Inflammation in Air Pouch Model:

Six to eight weeks old mice were used to generate air pouch as described previously [50]. Briefly, mice were injected subcutaneously with 5 ml of sterile air into the back to generate the air pouch. After 3 days another 3 ml of sterile air was injected into the pouch. 3 days later, 1 mg of CS in 500 μl of endotoxin-free PBS was injected into the air pouch. Control animals received only 500 μl of endotoxin-free PBS. 6 hours later animals were euthanized and air pouch was lavaged with 3 ml of PBS.

CS-Promotion of Implantable Lung Tumors:

LKR13 cells used in this study were kindly provided by Dr. Tyler Jacks [28]. To establish LKR13 tumors [51], 2×10$^6$ live LKR13 cells in presence of 2 mg CS particles were resuspended in 100 μl PBS, mixed with 100 μl matrigel (Corning) and injected subcutaneously into the right flank of naive six to eight weeks old BLT1$^{+/+}$Rag2$^{-/-}$ and BLT1$^{-/-}$ Rag2$^{-/-}$ mice. Mice injected subcutaneously with LKR13 cells alone served as controls. Tumor growth was monitored two to three times per week, and tumor size was measured in millimeters using a caliper. Average tumor size was calculated by measuring two perpendicular diameters. Animals bearing tumors were euthanized when tumors reached a size of 15 mm in one of the two perpendicular diameters or earlier if tumors ulcerated or animal showed signs of discomfort.

Lung Histopathology:

105 days old BLT1$^{+/+}$K-ras$^{LA1}$ and BLT1$^{-/-}$K-ras$^{LA1}$ mice were analyzed for lung tumor burden. Lungs were inflated with 10% buffered formalin and were then removed, fixed in 10% buffered formalin for 24 h and stored in 70% ethanol. Lung lobes were separated and processed, embedded in paraffin and serially sectioned. Mid-sagittal 5 µm serial lung sections (200 µm apart) were stained with haematoxylin and eosin and digitally scanned on Aperio ScanScope. Lung sections were analyzed by an experienced pulmonary pathologist. Lung lesions (hyperplasia-H, adenomatous hyperplasia-AH, and adenoma-A) based on the histological features [52] were enumerated on the entire lung section using the digital image. Digital images of lung sections were also used to analyze lung inflammation. Lung inflammation is quantified as the percentage of inflamed lung area to total lung area in H&E stained lung sections. Lung tissue macrophages in the sections were identified by immuno-histochemistry (IHC). Sections were stained with 1:50 diluted Rat anti-mouse F4/80 antibody (clone CL:A3-1, cat.#MCA497G, AbD Serotec) at the Pathology Core Research Laboratory at University of Louisville, following standard protocol. Five independent fields per mouse lung section were randomly selected for macrophage counting and average macrophages per field were represented. Crystalline silica particles in the lungs sections were viewed under polarized light and lungs were semi-quantitatively scored on a scale of 1-3 for the amount of deposited particles.

Immune Cell Identification by Flow Cytometry:

Leukocytes were collected from airways, air pouch or peritoneal cavity by lavage; from unlavaged whole lungs, LKR13 subcutaneous tumors, spleen or cultures of bone marrow derived macrophages, mast cells. Single cell suspension was obtained from whole lungs or subcutaneous tumors by digesting the tissue in an enzyme mixture consisting of collagenase A (2 mg/ml), DNase I (100 µg/ml) for 1 h at 37° C. with occasional vortexing. The digested tissue was filtered through a nylon mesh, and the resultant cells were washed twice in PBS. 2×10$^6$ cells in single-cell suspensions were incubated with F$_C$-receptor blocking antibody followed by staining with various cell surface marker antibodies from BD Biosciences (San Diego, Calif.) or Biolegend (San Diego, Calif.), following standard protocols. Flow cytometry data were acquired on FACS Calibur or FACS Canto (BD Biosciences) and analyzed using Flowjo software (Tree Star).

In the lung tissue and airways (BALF), leukocytes were identified as CD45$^+$ cells, alveolar or lung macrophages as CD45$^+$FSC$^{hi}$CD11c$^{hi}$ F4/80$^+$ cells, neutrophils as CD45$^+$ CD11c$^-$Ly6G$^{hi}$ Siglec-F$^-$ cells, B cells as CD45$^+$FSC$^{lo}$ B220$^+$ cells, CD4 cells as CD45$^+$FSC$^{lo}$ CD4$^+$ and CD8 cells as CD45$^+$FSC$^{lo}$CD8$^+$. In peritoneal cavity, macrophages were identified as CD45$^+$FSC$^{lo}$F4/80$^+$ cells and neutrophils as CD45$^+$SSC$^{hi}$Ly6G$^{hi}$ cells. In spleen B cells were CD45$^+$ FSC$^{lo}$ B220$^+$ and T cells were CD45$^+$FSC$^{lo}$ CD3$^+$. Macrophages from bone marrow cultures were CD11b$^+$F4/80+ and mast cells from bone marrow cultures were CD117$^+$FcεR1$^+$.

In the subcutaneous tumors, leukocytes were identified as CD45$^+$ cells, macrophages as CD45$^+$FSC$^{hi}$F4/80$^+$CD11b$^{hi}$ Ly6G$^{lo}$ cells, mast cells as CD45$^+$CD117$^+$FcεR1$^+$ and neutrophils as CD45$^+$SSC$^{hi}$Ly6G$^{hi}$ cells. In air pouch lavage fluid, leukocytes were identified as CD45$^+$ cells, macrophages as CD45$^+$FSC$^{hi}$ F4/80$^+$CD11b$^{hi}$ Ly6G$^{lo}$ cells and neutrophils as CD45$^+$SSC$^{hi}$Ly6G$^{hi}$ cells. Cytospin preparations of the air pouch lavage fluid cells were also done using Shandon Cytospin centrifuge (Shandon Lipshaw) followed by staining with Hema-3 reagents (Fisher Scientific) according to the manufacturer's recommendations.

Isolation of Lung Mast Cells and Alveolar Macrophages:

Cells obtained from pooled lung digests of 4 naïve WT (wild-type) mice were treated with RBC lysis buffer (BD Biosciences), resuspended in DMEM containing 10% FBS and incubated at 37° C. The non-adherent cells were transferred after 8 hours into fresh tubes without disturbing the adherent (macrophages and fibroblast) cells. The non-adherent cells were then incubated with F$_C$-receptor blocking antibody followed by staining for CD45, CD117 and FcεR1 in 5% BSA (Bovine serum albumin). Mast cells identified as FSC$^{hi}$ CD45$^+$CD117$^+$FcεR1$^+$ cells were sorted using BD FACS Aria III cell sorter. Purity of the cells was 95.3%.

Whole lung lavage from 10 naïve WT mice were pooled, resuspended in DMEM containing 10% FBS and incubated at 37° C. for 4 hours. The non-adherent cells were discarded and alveolar macrophages were obtained by dislodging the adherent cells, followed by staining for CD45 and F4/80 after blocking F$_C$-receptors. Purity of cells was 99.5%.

Isolation and Culture of Primary Murine Cells:

Bone marrow-derived mast cells (BMMC) were prepared from 6-8 weeks old mice of indicated genotypes. Briefly, bone marrow cells were flushed out and cultured in DMEM containing 10% FBS, 100 units/ml Penicillin, 100 µg/ml Streptomycin, 2 mM L-Glutamine, 50 µM β-mercaptoethanol supplemented with 12.5 ng/ml recombinant Mouse SCF (R&D #455 MC, 10 µg/ml Stock,) and 10 ng/ml recombinant Mouse IL-3 (R&D #403-ML, 10 µg/ml Stock). The bone marrow cells were plated at ~1×10$^6$/ml density in T-75 cm$^2$ flask containing 15 ml of medium. The non-adherent cells were transferred after 48 hours into fresh flasks without disturbing the adherent (fibroblast) cells. The flasks were changed weekly or as needed to separate the non-adherent mast cells from the contaminating adherent cells. The medium was changed once a week with medium containing SCF, IL-3. The homogenous population of mast cells was visible after 4 weeks of culture and propagated further for 4 weeks. The purity of BMMCs derived from WT or various KO (knock out) mice was confirmed to be ≥99% by surface staining for mast cell specific markers CD117 and FcεR1.

Bone marrow derived macrophages (BMDM) were prepared from 6-8 weeks old mice of indicated genotypes. Briefly, bone marrow cells were flushed out and cultured in DMEM containing 10% FBS, 100 units/ml Penicillin, 100 µg/ml Streptomycin, 2 mM L-Glutamine, 50 µM β-mercaptoethanol supplemented with 100 ng/ml recombinant Mouse MCSF (Biolegend). The bone marrow cells were plated at 0.6×10$^6$/ml density in 100 mm tissue culture dishes containing 10 ml of medium. After 3 days medium was replaced by 10 ml of fresh growth medium and a homogenous population of macrophages was visible. The cultures were maintained for another 3 days before stimulation. The cells were found to be more than 99% pure as confirmed by surface staining for F4/80 and CD11b. Eight weeks old mice were injected intraperitoneally with 2 ml of 3% aged thioglygollate medium. Peritoneum was lavaged after 10 h or 4 days to obtain elicited neutrophils and macrophages respectively. The purity of thioglycollate elicited neutrophils and macrophages; resident peritoneal macrophages were ≥95%.

For CS stimulation assays, mast cells from various sources were plated at 0.3 million per well of 12-well tissue culture dishes in 400 µl of medium without FBS. Primary macrophages from various sources, splenocytes and neutrophils were plated at 0.3 million per well of 12-well tissue culture dishes in 400 µl of 1% FBS containing medium. All primary cells were stimulated with 100 µg/cm$^2$ of CS for 6 h. Primary macrophages from all sources were primed with 10 ng/ml of LPS (InvivoGen) for 3 h prior to CS stimulation.

LKR13 and RAW264.7 cells were cultured in DMEM containing 10% FBS. For CS stimulation assays, 0.3 million cells were plated per well of 12-well tissue culture dishes in 400 µl of 1% FBS containing medium. The cells were stimulated for 6 h with 120 µg/cm$^2$ of CS. Whenever indicated RAW264.7 cells were pre-treated with 10 µM Zileuton (5-LO inhibitor) for 1 h.

Cell Migration Assay:

Chemotaxis of 300.19 cells and thioglycollate elicited peritoneal neutrophils was evaluated using 5-µm pore size Transwell filters (Corning Costar, Cambridge, Mass.). Briefly, 1 million cells in 100 µl of medium were loaded onto the upper chamber. The lower chamber was loaded with 600 µl of either medium alone or 0.3 nM LTB$_4$ or unstimulated RAW264.7 cell supernatants or 120 µg/cm$^2$ of CS stimulated RAW264.7 cell supernatants. After 3 h of incubation at 37° C. in 5% CO$_2$, the upper chamber was removed and cells that migrated to the lower chamber was counted.

LTB$_4$ and IL-1β Quantification:

Subcutaneous tumors were homogenized in 500 ul 1×PBS buffer containing 10 uM Indomethacin using Omni GLH general homogenizer. The homogenates were centrifuged at 14000 g for 10 min and LTB$_4$ levels in the supernatants were quantified. The LTB$_4$ levels were normalized to the amount of protein in the supernatants measured by Themo Sceintific Pierce BCA protein assay kit following manufacturer's instructions. LTB$_4$ in the tumor homogenate supernatant was expressed as pg/mg of protein. LTB$_4$ in cell culture supernatants, BALF, air pouch lavage and subcutaneous tumors was measured using LTB$_4$ EIA Kit (Cayman Chemical) according to the manufacturer's instructions. IL-1β in cell culture supernatants was measured using Mouse IL-1β ELISA MAX™ Standard Kit (Biolegend) according to the manufacturer's instructions.

Quantitative RT-PCR: Total RNA from LKR13 cells, bone marrow-derived macrophages and mast cells, subcutaneous tumors as well as lungs was isolated using an RNeasy Mini Kit (Qiagen) in accordance with the manufacturer's protocol. RNA samples were treated with DNase (Qiagen) before reverse transcription with TaqMan reverse transcription reagents (Applied Biosystems) using random hexamer primers. Quantitative PCR analyses were conducted as described previously [53] using 'power SYBR-green master mix' (Applied Biosystems). Expression of the target genes was normalized to GAPDH and the relative fold changes were calculated using the delta CT method. The fold changes were displayed relative to the PBS (vehicle) treated BLT1$^{+/+}$ samples or LKR13 injected BLT1$^{+/+}$Rag2$^{-/-}$ group. Data were representative of tissues isolated from at least 5 different mice for each cohort or triplicate cell cultures. The GAPDH, IL-1β, TNF-α, CXCL1, CXCL2, CXCL3, CXCL5, CCL2, CCL3, CCL4, CCL5, CXCR1, CXCR2 and CCR5 primers obtained from RealTimePrimers.com were used in this study.

Microarray and data analysis: Total RNA was prepared from mouse lung tissues as described above. The micro array was performed using Affymetrix GeneChip®Mouse Gene 1.0 ST Array according to manufacturer's protocol at the University of Louisville genomics facility. The GeneChip-brand array comprised of over 750,000 unique 25-mer oligonucleotide features constituting over 28,000 gene level probes with an average of 27 probes per gene. Briefly, Total RNA was amplified and labeled following the Affymetrix (Santa Clara, Calif.) standard protocol for whole transcript expression analysis, followed by hybridization to Affymetrix Mouse Gene 1.0 ST® arrays. The arrays were processed following the manufacturer recommended wash and stain protocol on an Affymetrix FS-450 fluidics station and scanned on an Affymetrix GeneChip® 7G scanner using Command Console 3.1. The resulting .cel files were imported into Partek Genomics Suite 6.6 and transcripts were normalized on a gene level using RMA as normalization and background correction method. Contrasts in a 1-way ANOVA were set up to compare the treatment groups of interest. The fold changes in gene expression along with Affymetrix IDs, p-values were uploaded on to MetaCore pathway analysis software. The fold change in cytokines, chemokines and their receptors were displayed relative to the PBS (vehicle) treated BLT1$^{+/+}$ sample and represented in graphs. Data were representative of pooled lung tissue RNA isolated from 3 different mice for each group. The data from the array analysis has been deposited in the NCBI public access database (http://www.ncbi.nlm.nih.gov/geo/query/acc.cgi?acc=GSE66985).

Multiplex Analysis:

Whole lung lavage fluids from PBS or CS treated BLT1$^{+/+}$ K-ras$^{LA1}$ and BLT1$^{-/-}$K-ras$^{LA1}$ or BLT1$^{+/+}$ and BLT1$^{-/-}$ mice were analyzed for levels of various inflammatory proteins namely TNF-α, CXCL1, CCL3, CCL4 and CCL5. The analysis was performed following standard protocols at the Proteomics core facility of Medical University of South Carolina.

Data analysis: All data are analyzed with GraphPad Prism4 Software, San Diego, Calif. and expressed as the means±s.e from at least three independent samples. Statistical difference among groups was analyzed using the Mann-Whitney U-test (in vivo) or Unpaired Student's t-test (in vitro/ex-vivo, RNA analysis). Two-tailed P values of <0.05 were considered as significant.

Example 2

This Example identifies how chemoattractants control leukocyte migration and inflammation with particular emphasis on leukotriene B$_4$ and its receptors BLT1 and BLT2. Mouse models were developed and novel reagents were generated to examine the function and regulation of BLT1 and BLT2. These models facilitated the identification that BLT1 is a critical mediator of inflammatory diseases including asthma (FIG. 17), atherosclerosis, arthritis and other autoimmune diseases as well as sleep apnea promoted atherogenesis (FIG. 18) and insulin resistance during diet induced obesity. BLT1 is also an important mediator of host response to infection and immune surveillance of intestinal cancers. Additionally, it is believed that absence of BLT1 reshapes the gut microbiome to promote colon cancer development (FIGS. 20-24). A diverse variety of cell types mediate these BLT1 effects, including, but not limited to, neutrophils (e.g., arthritis), macrophages (e.g., atherosclerosis, sleep apnea, and obesity induced inflammation), dendritic cells (e.g., sensitization phase of asthma), CD8$^+$ T-cells (e.g., effecter phase of asthma and antitumor immunity), and CD4+ and CD8+ T-cells (e.g., autoimmune uveitis).

Structure and Regulation of BLT1:

To study signaling pathways activated by BLT1, stable cell lines expressing native and mutant receptors and live cell video microscopy methods to monitor chemotaxis and receptor internalization in real time were developed [55, 56]. The present inventors showed that BLT1 couples to both Gi and Gq family of G-proteins. Whereas both types of G-proteins mediate calcium release and exocytosis in response to $LTB_4$, activation of Gi protein is essential for inducing pseudopod extension and chemotaxis [57]. Using RFP-labeled BLT1 and GFP labeled β-arrestin it was shown that phosphorylation of cytoplasmic serine/threonine residues regulate signaling but not β-arrestin association or internalization of BLT1 [58]. Computational methods were used to model BLT1 structure with and without $LTB_4$. This model allowed the identification of the $LTB_4$ ligand binding site and the activation mechanism of BLT1. The predicted ligand binding site and the mechanism of activation were fully validated by mutational analysis [59].

BLT1 in Inflammation:

The BLT1, BLT2 and BLT1/BLT2 double deficient mice were generated by targeted gene disruption [60-62]. These mice have been backcrossed onto C57B6, DBA-1, BALB/c and FVB backgrounds for various studies. Using the BLT1$^{-/-}$ mice to immunize with 300-19 cells stably expressing BLT1, the present inventors generated highly specific anti-murine BLT1 and anti-human BLT1 monoclonal antibodies (unpublished). The anti-murine BLT1 antibody has been extensively used to demonstrate regulation of BLT1 expression in various cell types in a variety of disease settings [62-66]. Initial results suggested that BLT1 is an important mediator of inflammation and showed unique sex dependent phenotype in platelet activating factor induced anaphylaxis [60]. An early and important discovery was that BLT1 can mediate transcriptional up regulation of genes involved in atherogenesis. Indeed, when the BLT1$^{-/-}$ mice were crossed onto Apo-E knockout background, the present inventors found substantial protection early during atherogenesis [67-69]. More recent studies in this area outline the critical importance of this pathway in sleep apnea promoted atherogenesis. Referring to FIGS. 18A-C, exposure of BLT1$^{+/+}$Apo-E$^{-/-}$ mice on a high fat diet to intermittent hypoxia substantially increased vascular lesions and this increase was completely abrogated in BLT1$^{-/-}$Apo-E$^{-/-}$ mice [70]. These results suggest that BLT1 could be an important target for drug development for complications associated with sleep apnea. Additionally, as illustrated in FIG. 17, BLT1 deficient mice are less susceptible to asthma than wild type mice. In other work, a role for BLT1 in development of airway hyper responsiveness was identified [71]. In this context, expression of BLT1 on dendritic cells is important in sensitization phase whereas expression on CD8+ T-cells is important in the effector phase of the disease [64, 65, 72].

BLT1 in Autoimmunity:

As illustrated in FIG. 19, BLT1$^{-/-}$ mice are completely protected from developing joint inflammation. In collagen induced arthritis models in C57B/6 mice, or in DBA-1 background (unpublished) the BLT1$^{-/-}$ mice showed no signs of joint inflammation despite making WT levels of auto (anti-collagen) antibodies [61, 73]. Consistent with this result, the BLT1$^{-/-}$ mice are also completely protected in a serum transfer model of arthritis [62]. In all cases neutrophils appear to be the primary cell responsible for disease progression [63]. In a model of auto reactive T-cell induced uveitis BLT1 expression on both T-cells and innate immune cells is critical for full disease development and absence of BLT1 is highly protective in ocular inflammation [74].

BLT1 in Cancer:

Chronic inflammation is known to promote many types of cancers. Since colon cancer is considered to be strongly promoted by inflammation, the present inventors crossed the BLT1$^{-/-}$ mice onto the Apc$^{Min/+}$ background to examine the role of the leukotriene pathway in the development of intestinal cancer. As with the other chronic inflammation promoted disease models, the present inventors anticipated protection from tumor development. However, a paradoxical increase in inflammation and tumor development in the BLT1$^{-/-}$Apc$^{Min/+}$ mice was observed (FIGS. 20-21). In a series of experiments, the present inventors identified that defects in host response in BLT1$^{-/-}$Apc$^{Min/+}$ mice translate into an altered gut microbiome (FIG. 22), increased MyD88 dependent inflammation and enhanced intestinal tumor development. Additionally, as illustrated in FIG. 23, the expression of bactericidal proteins is down regulated in BLT1$^{-/-}$Apc$^{Min/+}$ tumors.

While the absence of BLT1 accelerates colon cancer, Germ-free BLT1$^{-/-}$Apc$^{Min/+}$ mice are completely protected from colon cancer (manuscript in preparation), and BLT1 mediated CT1 migration is protective in colon and cervical cancers as well as melanomas (FIG. 24). The present inventors' previous studies have shown that in a cecal ligation and puncture model, the BLT1$^{-/-}$ mice harbored more bacterial loads but are protected from sepsis by limited second organ injury [75]. The present inventors' results from diverse mouse tumor models suggest that BLT1 is a critical mediator of anti-tumor immunity and immune surveillance. In this context, an early experiment showed that β-glucan mediated immunotherapy of tumors requires BLT1 expression on neutrophils [76]. Experiments in BLT1$^{-/-}$Apc$^{Min/+}$ as well as in a syngeneic implantable TC-1 cervical cancer model suggest that BLT1 expression on CD8+ T-cells is critical for generating anti-tumor immunity (unpublished).

BLT1 in Diet Induced Obesity:

In studying the role of BLT1 in diet induced obesity (DIO), the present inventors found that the BLT1$^{-/-}$ mice gained as much weight as the WT animals on a high fat diet [66] which selectively increases the circulating levels of CD11b+ monocytes. Absence of BLT1 skews the macrophages to an M2 like phenotype. Obese BLT1$^{-/-}$ mice were protected from systemic glucose and insulin intolerance (FIGS. 25A-D) and this was associated with a decrease in inflammation in adipose tissue and liver and a decrease in hepatic triglyceride accumulation. Deletion of BLT1 prevented high-fat induced loss of insulin signaling in liver and skeletal muscle. Current studies are aimed at establishing the efficacy of BLT1 inhibition in preventing or treating insulin resistance and identifying sequential diet associated changes in gut microbiota and the relationship of the microbiome to the development of insulin resistance.

BLT1 as a Target for Drug Development:

There has been considerable attention from the pharmaceutical industry on the leukotriene pathway as a target for rheumatoid arthritis, asthma and other inflammatory diseases. However, with the exception of $LTC_4$ antagonists (Montelukast, Pranlukast and Zafirlukast) no clear candidate drug has emerged from these studies. One simple reason for the lack of success could be that, in these studies, the pharmacology and drug development preceded molecular identification of the receptors. Historically, BLT1 was known to be a neutrophil receptor and many of the early development efforts were focused on this cell type. Over the last several years many discoveries from the present inventors' and other laboratories have expanded the LTB$_4$/BLT1 axis to many cell types and diverse array of inflammatory diseases. Therefore, the past failures might be related to the incomplete targeting and/or due to the mismatch of compounds to the indications as well as issues related to the design of clinical trials.

Based on all the new data in animal models, the present inventors believe that BLT1 is still a valid target for drug development, including, for example, in the areas of insulin resistance leading to a pre diabetic condition and in development of immune therapies for treatment of certain cancers. As novel information becomes available in DIO, sleep apnea promoted atherogenesis, cancer, arthritis, asthma and other inflammatory conditions; development of new compounds for these indications will be an essential first step in retargeting this pathway. In this context, receptors might be better targets than LTB$_4$ biosynthetic enzymes because the latter could alter homeostasis and enhance the generation COX derived inflammatory mediators. The BLT1$^{-/-}$ mice did not display any spontaneous phenotypes and have a normal life span suggesting that they are not immune compromised. This would be an important consideration for developing treatments for chronic diseases as most currently available anti-inflammatory drugs could lead to immune deficiency negating their benefits. The present inventors' as yet unpublished work suggests strong host dependent changes in gut microbiota. Since gut flora have been implicated in obesity it would be important to delineate the changes in microbiota during high fat feeding of WT and BLT1$^{-/-}$ mice as well as WT mice treated with new BLT1 antagonists. Using structure based virtual screening strategies many novel compounds that are agonists and/or antagonists to BLT1 were identified (unpublished data).

Throughout this document, various references are mentioned. All such references are incorporated herein by reference, including the references set forth in the following list:

REFERENCES

1. Mantovani, A., et al., *Cancer-related inflammation.* Nature, 2008. 454(7203): p. 436-44.
2. Houghton, A. M., *Mechanistic links between COPD and lung cancer.* Nat Rev Cancer, 2013. 13(4): p. 233-45.
3. Colotta, F., et al., *Cancer-related inflammation, the seventh hallmark of cancer: links to genetic instability.* Carcinogenesis, 2009. 30(7): p. 1073-81.
4. Russo, M., F. Di Nicolantonio, and A. Bardelli, *Climbing RAS, the everest of oncogenes.* Cancer Discov, 2014. 4(1): p. 19-21.
5. Ji, H., et al., *K-ras activation generates an inflammatory response in lung tumors.* Oncogene, 2006. 25(14): p. 2105-12.
6. Elinav, E., et al., *Inflammation-induced cancer: crosstalk between tumours, immune cells and microorganisms.* Nat Rev Cancer, 2013. 13(11): p. 759-71.
7. Takahashi, H., et al., *Tobacco smoke promotes lung tumorigenesis by triggering IKKbeta- and JNK1-dependent inflammation.* Cancer Cell, 2010. 17(1): p. 89-97.
8. Leung, C. C., I. T. Yu, and W. Chen, *Silicosis.* Lancet, 2012. 379(9830): p. 2008-18.
9. Huaux, F., *New developments in the understanding of immunology in silicosis.* Current opinion in allergy and clinical immunology, 2007. 7(2): p. 168-73.
10. Takato, H., et al., *The specific chymase inhibitor TY-51469 suppresses the accumulation of neutrophils in the lung and reduces silica-induced pulmonary fibrosis in mice.* Exp Lung Res, 2011. 37(2): p. 101-8.
11. Brown, T., *Silica exposure, smoking, silicosis and lung cancer—complex interactions.* Occup Med (Lond), 2009. 59(2): p. 89-95.
12. Cox, L. A., Jr., *An exposure-response threshold for lung diseases and lung cancer caused by crystalline silica.* Risk Anal, 2011. 31(10): p. 1543-60.
13. Liu, Y., et al., *Exposure-response analysis and risk assessment for lung cancer in relationship to silica exposure: a 44-year cohort study of 34,018 workers.* Am J Epidemiol, 2013. 178(9): p. 1424-33.
14. Kachuri, L., et al., *Occupational exposure to crystalline silica and the risk of lung cancer in Canadian men.* Int J Cancer, 2013.
15. Balkwill, F., *Cancer and the chemokine network.* Nat Rev Cancer, 2004. 4(7): p. 540-50.
16. Ruffini, P. A., et al., *Manipulating the chemokine-chemokine receptor network to treat cancer.* Cancer, 2007. 109(12): p. 2392-404.
17. Oyoshi, M. K., et al., *Leukotriene B4-driven neutrophil recruitment to the skin is essential for allergic skin inflammation.* Immunity, 2012. 37(4): p. 747-58.
18. Li, R. C., et al., *Leukotriene B4 Receptor-1 Mediates Intermittent Hypoxia-induced Atherogenesis.* American journal of respiratory and critical care medicine, 2011. 184(1): p. 124-31.
19. Spite, M., et al., *Deficiency of the Leukotriene B4 Receptor, BLT-1, Protects against Systemic Insulin Resistance in Diet-Induced Obesity.* Journal of immunology, 2011.
20. Chou, R. C., et al., *Lipid-cytokine-chemokine cascade drives neutrophil recruitment in a murine model of inflammatory arthritis.* Immunity, 2010. 33(2): p. 266-78.
21. Johnson, L., et al., *Somatic activation of the K-ras oncogene causes early onset lung cancer in mice.* Nature, 2001. 410(6832): p. 1111-6.
22. Houghton, A. M., et al., *Neutrophil elastase-mediated degradation of IRS-1 accelerates lung tumor growth.* Nature medicine, 2010. 16(2): p. 219-23.
23. Gong, L., et al., *Promoting effect of neutrophils on lung tumorigenesis is mediated by CXCR2 and neutrophil elastase.* Mol Cancer, 2013. 12(1): p. 154.
24. Wislez, M., et al., *High expression of ligands for chemokine receptor CXCR2 in alveolar epithelial neoplasia induced by oncogenic kras.* Cancer Res, 2006. 66(8): p. 4198-207.
25. Grivennikov, S. I., F. R. Greten, and M. Karin, *Immunity, inflammation, and cancer.* Cell, 2010. 140(6): p. 883-99.
26. Brown, J. M., et al., *Silica-directed mast cell activation is enhanced by scavenger receptors.* Am J Respir Cell Mol Biol, 2007. 36(1): p. 43-52.
27. Colville-Nash, P. and T. Lawrence, *Air pouch models of inflammation and modifications for the study of granuloma-mediated cartilage degradation.* Methods Mol Biol, 2003. 225: p. 181-9.
28. Wislez, M., et al., *High expression of ligands for chemokine receptor CXCR2 in alveolar epithelial neoplasia induced by oncogenic kras.* Cancer research, 2006. 66(8): p. 4198-207.
29. Bode, C., et al., *Suppressive oligodeoxynucleotides reduce lung cancer susceptibility in mice with silicosis.* Carcinogenesis, 2014. 35(5): p. 1078-83.

30. Hamilton, R. F., Jr., S. A. Thakur, and A. Holian, *Silica binding and toxicity in alveolar macrophages*. Free Radic Biol Med, 2008. 44(7): p. 1246-58.
31. Suzuki, N., et al., *Mast cells are essential for the full development of silica-induced pulmonary inflammation: a study with mast cell-deficient mice*. Am J Respir Cell Mol Biol, 1993. 9(5): p. 475-83.
32. Beamer, C. A., et al., *Innate immune processes are sufficient for driving silicosis in mice*. J Leukoc Biol, 2010. 88(3): p. 547-57.
33. Piguet, P. F., et al., *Requirement of tumour necrosis factor for development of silica-induced pulmonary fibrosis*. Nature, 1990. 344(6263): p. 245-7.
34. Yao, S. Q., et al., *Role of Fas/FasL pathway-mediated alveolar macrophages releasing inflammatory cytokines in human silicosis*. Biomed Environ Sci, 2013. 26(11): p. 930-3.
35. Chen, Y., et al., *Neutralization of interleukin-17A delays progression of silica-induced lung inflammation and fibrosis in C57BL/6 mice*. Toxicol Appl Pharmacol, 2014. 275(1): p. 62-72.
36. Cassel, S. L., et al., *The Nalp3 inflammasome is essential for the development of silicosis*. Proc Natl Acad Sci USA, 2008. 105(26): p. 9035-40.
37. Wang, X., et al., *Silencing CD36 gene expression results in the inhibition of latent-TGF-beta1 activation and suppression of silica-induced lung fibrosis in the rat*. Respir Res, 2009. 10: p. 36.
38. Dostert, C., et al., *Innate immune activation through Nalp3 inflammasome sensing of asbestos and silica*. Science, 2008. 320(5876): p. 674-7.
39. Guo, J., et al., *Neutralization of interleukin-1 beta attenuates silica-induced lung inflammation and fibrosis in C57BL/6 mice*. Arch Toxicol, 2013. 87(11): p. 1963-73.
40. Hornung, V., et al., *Silica crystals and aluminum salts activate the NALP3 inflammasome through phagosomal destabilization*. Nature immunology, 2008. 9(8): p. 847-56.
41. Lammermann, T., et al., *Neutrophil swarms require LTB4 and integrins at sites of cell death in vivo*. Nature, 2013. 498(7454): p. 371-5.
42. Fridlender, Z. G. and S. M. Albelda, *Tumor-associated neutrophils: friend or foe?* Carcinogenesis, 2012. 33(5): p. 949-55.
43. Gregory, A. D. and A. M. Houghton, *Tumor-associated neutrophils: new targets for cancer therapy*. Cancer Res, 2011. 71(7): p. 2411-6.
44. Mantovani, A., et al., *Neutrophils in the activation and regulation of innate and adaptive immunity*. Nat Rev Immunol, 2011. 11(8): p. 519-31.
45. Shang, K., et al., *Crucial involvement of tumor-associated neutrophils in the regulation of chronic colitis-associated carcinogenesis in mice*. PLoS One, 2012. 7(12): p. e51848.
46. Tazzyman, S., et al., *Inhibition of neutrophil infiltration into A549 lung tumors in vitro and in vivo using a CXCR2-specific antagonist is associated with reduced tumor growth*. Int J Cancer, 2011. 129(4): p. 847-58.
47. Ilie, M., et al., *Predictive clinical outcome of the intratumoral CD66b-positive neutrophil-to-CD8-positive T-cell ratio in patients with resectable nonsmall cell lung cancer*. Cancer, 2012. 118(6): p. 1726-37.
48. Carpagnano, G. E., et al., *Neutrophilic airways inflammation in lung cancer: the role of exhaled LTB-4 and IL-8*. BMC Cancer, 2011. 11: p. 226.
49. Haribabu, B., et al., *Targeted disruption of the leukotriene B(4) receptor in mice reveals its role in inflammation and platelet-activating factor-induced anaphylaxis*. J Exp Med, 2000. 192(3): p. 433-8.
50. Sin, Y. M., et al., *Mast cells in newly formed lining tissue during acute inflammation: a six day air pouch model in the mouse*. Ann Rheum Dis, 1986. 45(10): p. 873-7.
51. Zhang, L., et al., *A novel immunocompetent murine model for replicating oncolytic adenoviral therapy*. Cancer Gene Ther, 2015. 22(1): p. 17-22.
52. Nikitin, A. Y., et al., *Classification of proliferative pulmonary lesions of the mouse: recommendations of the mouse models of human cancers consortium*. Cancer research, 2004. 64(7): p. 2307-16.
53. Mathis, S. P., et al., *Nonredundant roles for leukotriene B4 receptors BLT1 and BLT2 in inflammatory arthritis*. J Immunol, 2010. 185(5): p. 3049-56.
54. Hicks, A., et al., *Leukotriene $B_4$ receptor antagonists as therapeutics for inflammatory disease: preclinical and clinical development*. Expert Opin. Investig. Drugs, 2007. 16 (12): p. 1909-1920.
55. Jala, V. R. and B. Haribabu, Real-time analysis of G protein-coupled receptor signaling in live cells. *Methods Mol Biol,* 2006. 332: p. 159-65.
56. Jala, V. R. and B. Haribabu, Real-time imaging of leukotriene B mediated cell migration and BLT1 interactions with beta-arrestin. *J Vis Exp,* 2010(46).
57. Haribabu, B., D. V. Zhelev, B. C. Pridgen, R. M. Richardson, H. Ali, and R. Snyderman, Chemoattractant receptors activate distinct pathways for chemotaxis and secretion. Role of G-protein usage. *J Biol Chem,* 1999. 274(52): p. 37087-92.
58. Jala, V. R., W. H. Shao, and B. Haribabu, Phosphorylation-independent beta-arrestin translocation and internalization of leukotriene B4 receptors. *J Biol Chem,* 2005. 280(6): p. 4880-7.
59. Basu, S., V. R. Jala, S. Mathis, S. T. Rajagopal, A. Del Prete, P. Maturu, J. O. Trent, and B. Haribabu, Critical role for polar residues in coupling leukotriene B4 binding to signal transduction in BLT1. *J Biol Chem,* 2007. 282(13): p. 10005-17.
60. Haribabu, B., M. W. Verghese, D. A. Steeber, D. D. Sellars, C. B. Bock, and R. Snyderman, Targeted disruption of the leukotriene B(4) receptor in mice reveals its role in inflammation and platelet-activating factor-induced anaphylaxis, *J Exp Med,* 2000. 192(3): p. 433-8.
61. Shao, W. H., A. Del Prete, C. B. Bock, and B. Haribabu, Targeted disruption of leukotriene B4 receptors BLT1 and BLT2: a critical role for BLT1 in collagen-induced arthritis in mice, *J Immunol,* 2006. 176(10): p. 6254-61.
62. Mathis, S. P., V. R. Jala, D. M. Lee, and B. Haribabu, Nonredundant roles for leukotriene B4 receptors BLT1 and BLT2 in inflammatory arthritis. *J Immunol,* 2010. 185(5): p. 3049-56.
63. Chou, R. C., N. D. Kim, C. D. Sadik, E. Seung, Y. Lan, M. H. Byrne, B. Haribabu, Y. Iwakura, and A. D. Luster, Lipid-cytokine-chemokine cascade drives neutrophil recruitment in a murine model of inflammatory arthritis. *Immunity,* 2010. 33(2): p. 266-78.
64. Miyahara, N., H. Ohnishi, H. Matsuda, S. Miyahara, K. Takeda, T. Koya, S. Matsubara, M. Okamoto, A. Dakhama, B. Haribabu, and E. W. Gelfand, Leukotriene B4 receptor 1 expression on dendritic cells is required for the development of Th2 responses and allergen-induced airway hyperresponsiveness. *J Immunol,* 2008. 181(2): p. 1170-8.
65. Ohnishi, H., N. Miyahara, A. Dakhama, K. Takeda, S. Mathis, B. Haribabu, and E. W. Gelfand, Corticosteroids enhance CD8+ T cell-mediated airway hyperresponsiveness and allergic inflammation by upregulating leukotriene B4 receptor 1. *J Allergy Clin Immunol,* 2008. 121(4): p. 864-71 e4.
66. Spite, M., J. Hellmann, Y. Tang, S. P. Mathis, M. Kosuri, A. Bhatnagar, V. R. Jala, and B. Haribabu, Deficiency of the leukotriene B4 receptor, BLT-1, protects against systemic insulin resistance in diet-induced obesity. *J Immunol,* 2011. 187(4): p. 1942-9.
67. Haribabu, B., Leukotrienes: Novel targets for vascular disease. *Discov Med,* 2004. 4(23): p. 281-7.
68. Jala, V. R. and B. Haribabu, Leukotrienes and atherosclerosis: new roles for old mediators. *Trends Immunol,* 2004. 25(6): p. 315-22.
69. Subbarao, K., V. R. Jala, S. Mathis, J. Suttles, W. Zacharias, J. Ahamed, H. Ali, M. T. Tseng, and B. Haribabu, Role of leukotriene B4 receptors in the development of atherosclerosis: potential mechanisms. *Arterioscler Thromb Vasc Biol,* 2004. 24(2): p. 369-75.
70. Li, R. C., B. Haribabu, S. P. Mathis, J. Kim, and D. Gozal, Leukotriene B4 receptor-1 mediates intermittent hypoxia-induced atherogenesis. *Am J Respir Crit Care Med,* 2011. 184(1): p. 124-31.
71. Miyahara, N., K. Takeda, S. Miyahara, S. Matsubara, T. Koya, A. Joetham, E. Krishnan, A. Dakhama, B. Haribabu, and E. W. Gelfand, Requirement for leukotriene B4 receptor 1 in allergen-induced airway hyperresponsiveness. *Am J Respir Crit Care Med,* 2005. 172(2): p. 161-7.
72. Del Prete, A., W. H. Shao, S. Mitola, G. Santoro, S. Sozzani, and B. Haribabu, Regulation of dendritic cell migration and adaptive immune response by leukotriene B4 receptors: a role for LTB4 in up-regulation of CCR7 expression and function. *Blood,* 2007. 109(2): p. 626-31.
73. Mathis, S., V. R. Jala, and B. Haribabu, Role of leukotriene B4 receptors in rheumatoid arthritis. *Autoimmun Rev,* 2007. 7(1): p. 12-7.
74. Liao, T., Y. Ke, W. H. Shao, B. Haribabu, H. J. Kaplan, D. Sun, and H. Shao, Blockade of the interaction of leukotriene b4 with its receptor prevents development of autoimmune uveitis. *Invest Ophthalmol Vis Sci,* 2006. 47(4): p. 1543-9.
75. Scott, M. J., W. G. Cheadle, J. J. Hoth, J. C. Peyton, K. Subbarao, W. H. Shao, and B. Haribabu, Leukotriene B4 receptor (BLT-1) modulates neutrophil influx into the peritoneum but not the lung and liver during surgically induced bacterial peritonitis in mice. *Clin Diagn Lab Immunol,* 2004. 11(5): p. 936-41.
76. Allendorf, D. J., J. Yan, G. D. Ross, R. D. Hansen, J. T. Baran, K. Subbarao, L. Wang, and B. Haribabu, C5a-mediated leukotriene B4-amplified neutrophil chemotaxis is essential in tumor immunotherapy facilitated by antitumor monoclonal antibody and beta-glucan. *J Immunol,* 2005. 174(11): p. 7050-6.

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for treating an inflammatory disease, comprising administering an effective amount of a BLT1 inhibitor to a subject in need thereof, wherein the inflammatory disease is selected from the group consisting of silicosis, lung cancer, and combinations thereof, wherein the subject has been exposed to the irritant crystalline silicate.

2. The method of claim 1, wherein the BLT1 inhibitor is a BLT1 antagonist.

3. The method of claim 1, wherein the inhibitor is a small molecule or a polypeptide.

4. The method of claim 1, wherein the inhibitor is an siRNA.

5. The method of claim 1, wherein the inhibitor is provided in a pharmaceutical composition that comprises a pharmaceutically acceptable carrier.

6. The method of claim 1, wherein the subject has been diagnosed with the inflammatory disease.

7. The method of claim 1, wherein the subject is at risk for developing the inflammatory disease.

8. A method for treating an inflammatory disease, comprising:
   administering an effective amount of a BLT1 inhibitor to a subject in need thereof;
   wherein the inflammatory disease is selected from the group consisting of silicosis, lung cancer, and combinations thereof; and
   wherein the BLT1 inhibitor is selected from the group consisting of a BLT1 antagonist, a small molecule, a polypeptide, an siRNA, and combinations thereof;
   wherein the subject has been exposed to crystalline silica.

* * * * *